United States Patent
Kobuke et al.

(10) Patent No.: US 6,602,998 B2
(45) Date of Patent: Aug. 5, 2003

(54) MERCAPTO-SUBSTITUTED IMIDAZOLYLPORPHYRIN METAL COMPLEX MONOMER, POLYMER HAVING THE SAME AS A REPEATING UNIT AND METHOD OF PREPARING THE SAME

(75) Inventors: Yoshiaki Kobuke, Ikoma (JP); Kazuya Ogawa, Ikoma (JP)

(73) Assignee: Nara Institute of Science and Technology, Ikoma (JP)

( * ) Notice: Subject to any disclaimer, the term of this patent is extended or adjusted under 35 U.S.C. 154(b) by 44 days.

(21) Appl. No.: 09/802,923

(22) Filed: Mar. 12, 2001

(65) Prior Publication Data

US 2001/0027252 A1 Oct. 4, 2001

(30) Foreign Application Priority Data

Mar. 13, 2000 (JP) ........................................ 2000-068766

(51) Int. Cl.$^7$ ............................................ C07D 487/22
(52) U.S. Cl. ....................................................... 540/145
(58) Field of Search ......................................... 540/145

(56) References Cited

PUBLICATIONS

Kohei Uosaki, et al., "Very Efficient Visible–Light–Induced Uphill Electron Transfer at a Self–Assembled Monolayer with a Porphyrin–Ferrocene–Thiol Linked Molecule," J. Am. Chem. Soc., 119, 1997, pp. 8367–8368.
Hiroshi Imahori, et al., "Photoactive Three–Dimensional Monolayers:Porphyrin–Alkanethiolate–Stabilized Gold Clusters," J. Am. Chem. Soc., 123, 2001, pp. 335–336.
Hiroshi Imahori, et al., "Light–Harvesting and Photocurrent Generation by Gold Electrodes Modified with Mixed Self–Assembled Monolayers of Boron–Dipyrrin and Ferrocene–Porphyrin–Fullerene Triad," J. Am. Chem. Soc., 123, 2001, pp. 100–110.
Hiroshi Imahori, et al., "Chain Length Effect on the Structure and Photoelectrochemical Properties of Self–Assembled Monolayers of Porphyrins on Gold Electrodes," J. Phys. Chem. B, 104, 2000, pp. 1253–1260.
Daniel T. Gryko, et al., "Thiol–Derivatized Porphyrins for Attachment to Electroactive Surfaces," J. Org. Chem., 64, 1999, pp. 8635–8647.

*Primary Examiner*—John M. Ford
(74) *Attorney, Agent, or Firm*—Oblon, Spivak, McClelland, Maier & Neustadt, P.C.

(57) ABSTRACT

A mercapto-substituted imidazolylporphyrin metal complex monomer represented by a general formula (1):

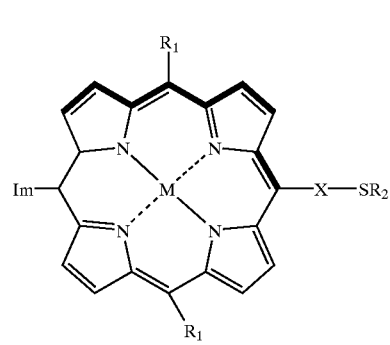

(1)

wherein $R_1$ represents a group selected from the group consisting of an alkyl group, unsubstituted aryl group, alkyl-substituted aryl group and alkyloxy-substituted aryl group, M represents a metal ion selected from the group consisting of Zn(II), Ga(III), Fe(II), Co(II), and Ru(II), X represents a divalent linking group containing at least one group selected from the group consisting of an arylene group and an alkylene group, $R_2$ represents a hydrogen atom or an acetyl group, and Im represents $Im_1$ or $Im_2$ set forth below:

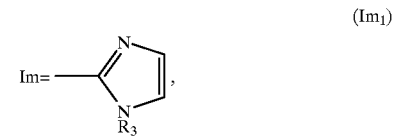

($Im_1$)

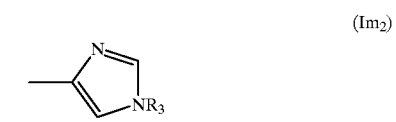

($Im_2$)

wherein $R_3$ represents a hydrogen atom or an alkyl group.

16 Claims, 2 Drawing Sheets

MERCAPTO-SUBSTITUTED IMIDAZOLYLPORPHYRIN METAL COMPLEX MONOMER, POLYMER HAVING THE SAME AS A REPEATING UNIT AND METHOD OF PREPARING THE SAME

CROSS-REFERENCE TO RELATED APPLICATIONS

This application is based upon and claims the benefit of priority from the prior Japanese Patent Application No. 2000-068766, filed Mar. 13, 2000, the entire contents of which are incorporated herein by reference.

BACKGROUND OF THE INVENTION

The present invention relates to a novel porphyrin metal complex and a method of preparing the same. More specifically, the present invention is concerned with a mercapto-substituted imidazolylporphyrin metal complex monomer and a polymer having the monomer as a constitutional unit, and methods of preparing the monomer and the polymer. The polymer provided by the invention is capable of being connected to an electrode via the mercapto group contained in the polymer.

The polymer having the porphyrin metal complex monomer of the present invention as a constitutional unit, may be used as energy transfer devices for transferring photonic energy and electronic energy of the order of nano-meter to sub-micrometer. More specifically, the polymer having the porphyrin metal complex of the present invention as a constitutional unit is applicable to materials for use in artificial photosynthesis systems, solar batteries, and the like.

The porphyrin metal complex is constituted by four pyrrole nuclei, four methine groups and a metal ion. Each two of the four pyrrole nuclei is cross-linked by one methine group to form cyclic tetrapyrrole, and a metal ion is inserted into the center of the cyclic tetrapyrrole. The porphyrin ring, when one of its double bonds is reduced, is referred to as "chlorin". When a magnesium (II) is inserted as a central metal ion in the chlorin skeleton, the resultant structure is called chlorophyll. Chlorophyll is used in a photosynthetic protein system, where it serves as an antenna complex for trapping and transferring photonic energy and also serves as a special pair and pheophytin, into which no metal ion is inserted, responsible for electron transfer. And then, electrons are finally transferred to benzoquinonyl and stored therein.

The electric wire constructed at a molecular level is important since it may be used in photovoltaic devices or photosynthetic systems for transferring electrons and energy. From this point of view, various studies have been made. Since the porphyrin metal complex has characteristics exhibited by conjugated π electrons, it is suitable for a material which forms a molecular-level electric wire. There have been some reports on the porphyrin connected to a gold electrode or the like.

For example, Sakata et al. have reported that a porphyrin unit is self-organized over the surface of gold via a thiol group (Chem. Lett. 1447 (1994), Chem. Lett. 907 (1996), Chem. Commun. 57 (1998), Chem. Lett. 267 (1988)). Although they perform electrochemical measurements and experiments on photoirradiation on the surface of the gold electrode, they fail to develop an electric wire of the porphyrin polymer. Lindsey et al., have recently succeeded in synthesizing a porphyrin monomer using a thiol derivative as a substituent (J. Org. Chem, 64, 8635 (1999)). The use of the thiol derivative provided an interesting finding: an acetyl derivative can be connected onto the surface of gold but a pivaloyl group cannot. However, the porphyrin polymerization through covalent bonds have not yet been attained. There are two problems in forming the porphyrin polymer by a covalent bond and using it as a wire. First, much time and effort are required for polymerization and purification of the porphyrin polymer. Second, it is difficult to reconstruct or cleave the polymer array. It has not yet been reported that the wire of the porphyrin polymer has been successfully developed. On the other hand, Takahashi et al., have studied porphyrin in an attempt to use it as a material for a solar battery (J. Phys. Chem. B, 103, 4868 (1999), J. Phys. Chem. B, 101, 991 (1997), J. Phys. Chem, 91, 3055 (1987)). They employ a simple porphyrin compound or a mixture thereof. As a result, they attained a photocurrent rate of a maximum 18.9%. However, the solar battery admits further improvement in a method of connecting the wire to an electrode and in selection of porphyrin compound to be employed in the wire.

BRIEF SUMMARY OF THE INVENTION

An object of the present invention is to provide a device in a length of tens to hundreds nanometer for transferring photonic energy and electronic energy, which is expected to be applied into artificial photosynthesis and novel materials for solar batteries. More specifically, the object of the present invention is to provide a device of a self-organized type, which is capable of connecting tightly and stably to a surface of an electrode and which is easy to cleave and reconstructed.

Another object of the present invention is to provide a method of preparing the aforementioned device.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

Figure 1:
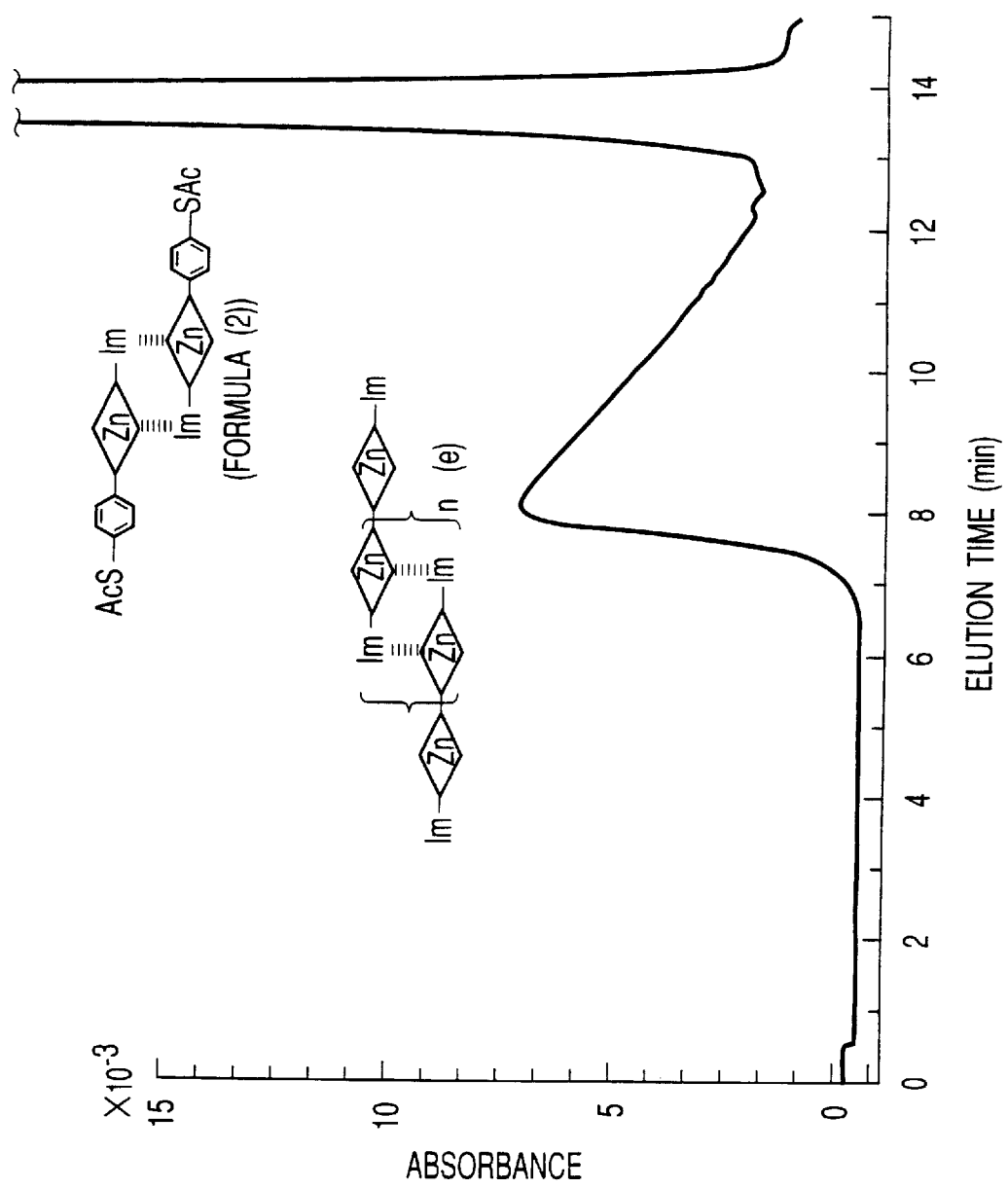
FIG. 1 is a chromatogram of a solution containing the poly(porphyrin) of the formula (e) and a dimer of an acetylthiophenyl-imidazolylporphyrin zinc complex represented by a general formula (2) at a ratio of 5:1 in ethanol-free chloroform, where the poly(porphyrin) has a molecular-weight distribution having a peak at 100,000 and extending to 500,000.

The present inventors have conducted intensive and extensive studies to attain the aforementioned object. As a result, they developed imidazolylporphyrin that is constructed of a porphyrin metal complex to which a specific imidazolyl group and a specific mercapto group are attached. The inventors also found that when a polymer is formed of the imidazolylporphyrin as a constitution unit, the aforementioned objects can be attained. In this way, the present invention was accomplished, and provide the following compounds and methods for preparing the compounds:

(1) A mercapto-substituted imidazolylporphyrin metal complex monomer represented by a general formula (1):

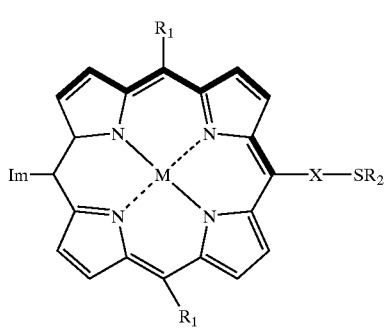

(1)

wherein $R_1$ represents a group selected from the group consisting of an alkyl group, unsubstituted aryl group, alkyl-substituted aryl group and alkyloxy-substituted aryl group; M represents a metal ion selected from the group consisting of Zn(II), Ga(III), Fe(II), Co(II), and Ru(II); X represents a divalent linking group containing at least one group selected from the group consisting of an arylene group and an alkylene group; $R_2$ represents a hydrogen atom or an acetyl group; and Im represents $Im_1$ or $Im_2$ set forth below:

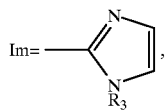

(Im$_1$)

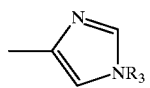

(Im$_2$)

wherein $R_3$ represents a hydrogen atom or an alkyl group.

(2) The mercapto-substituted imidazolylporphyrin metal complex monomer represented by the general formula (1) according to item (1) above, wherein $R_1$ represents a group selected from the group consisting of an alkyl group having 3–20 carbon atoms, aryl group having 6–20 carbon atoms, alkyl-substituted aryl group having 7–24 carbon atoms and alkyloxy-substituted aryl group having 7–24 carbon atoms;

X represents a divalent linking group containing at least one group selected from the group consisting of —$(CH_2)_n$— (wherein n represents an integer of 1–17) and an arylene group having 6–14 carbon atoms.

(3) The mercapto-substituted imidazolylporphyrin metal complex monomer represented by the general formula (1) according to item (1) or (2) above, wherein $R_1$ is an alkyl group having 3–20 carbon atoms; M is Zn ion; 2 $R_2$ is an acetyl group; and Im is $Im_1$ (wherein $R_3$ is a methyl group).

(4) A mercapto-substituted imidazolylporphyrin metal complex dimer represented by a general formula (2):

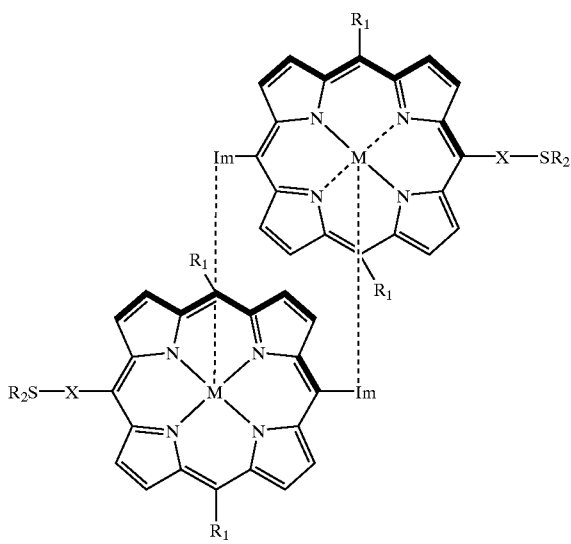

(2)

wherein each of $R_1$, M, $R_2$, X and Im including $R_3$ has the same meaning as defined for the general formula (1) mentioned in item (1) above.

(5) The mercapto-substituted imidazolylporphyrin metal complex dimer according to item (4) above, wherein $R_1$ represents a group selected from the group consisting of an alkyl group having 3–20 carbon atoms, aryl group having 6–20 carbon atoms, alkyl-substituted aryl group having 7–24 carbon atoms and alkyloxy-substituted aryl group having 7–24 carbon atoms; X represents a divalent linking group containing at least one group selected from the group consisting of —$(CH_2)_n$— (wherein n represents an integer of 1–17) and an arylene group having 6–14 carbon atoms.

(6) The mercapto-substituted imidazolylporphyrin metal complex dimer according to item (4) or (5) above, wherein $R_1$ is an alkyl group having 3–20 carbon atoms; M is Zn ion; X is a phenylene group; $R_2$ is an acetyl group; and Im is $Im_1$ (wherein $R_3$ is a methyl group).

(7) A poly(imidazolylporphyrin metal complex) having a mercapto group at both ends thereof, which is represented by a general formula (3):

(3)

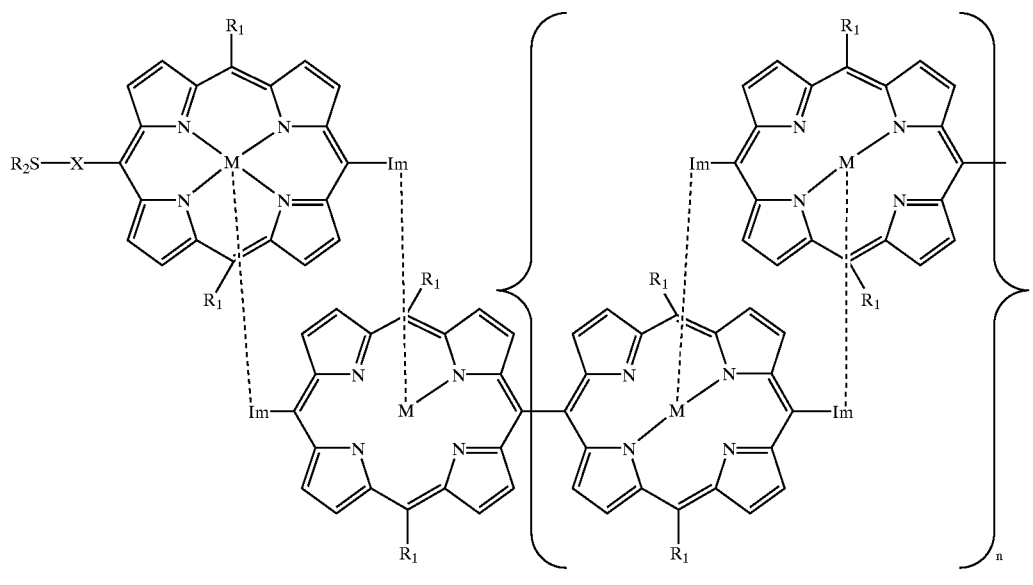

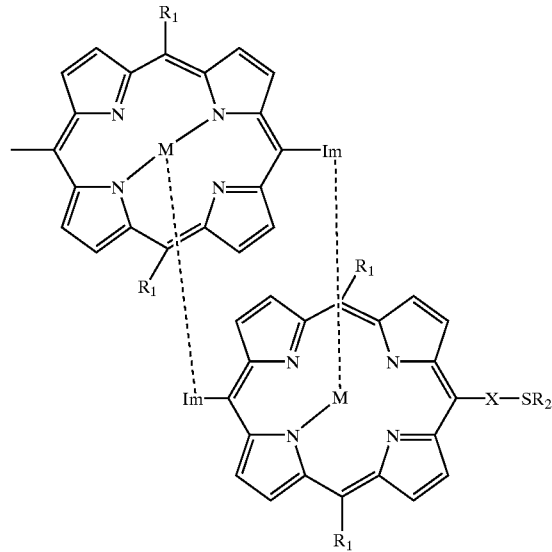

wherein each of $R_1$, M, $R_2$, X and Im including $R_3$ has the same meaning as defined in item (1) above; and n represents an integer of 0 or more.

(8) The poly(imidazolylporphyrin metal complex) represented by the general formula (3) according to item (7) above, wherein $R_1$ represents a group selected from the group consisting of an alkyl group having 3–20 carbon atoms, aryl group having 6–20 carbon atoms, alkyl-substituted aryl group having 7–24 carbon atoms and alkyloxy-substituted aryl group having 7–24 carbon atoms; X represents a divalent linking group containing at least one group selected from the group consisting of —$(CH_2)_n$— (wherein n represents an integer of 1–17) and an arylene group having 6–14 carbon atoms.

(9) The poly(imidazolylporphyrin metal complex) represented by the general formula (3) according to item (8) above, wherein $R_1$ is an alkyl group having 3–20 carbon atoms; M is Zn ion; X is a phenylene group; $R_2$ is an acetyl group; and Im is $Im_1$ (wherein $R_3$ is a methyl group).

(10) A poly(imidazolylporphyrin metal complex) having a mercapto group at one end and a quinonyl group at the other end, which is represented by a general formula (4):

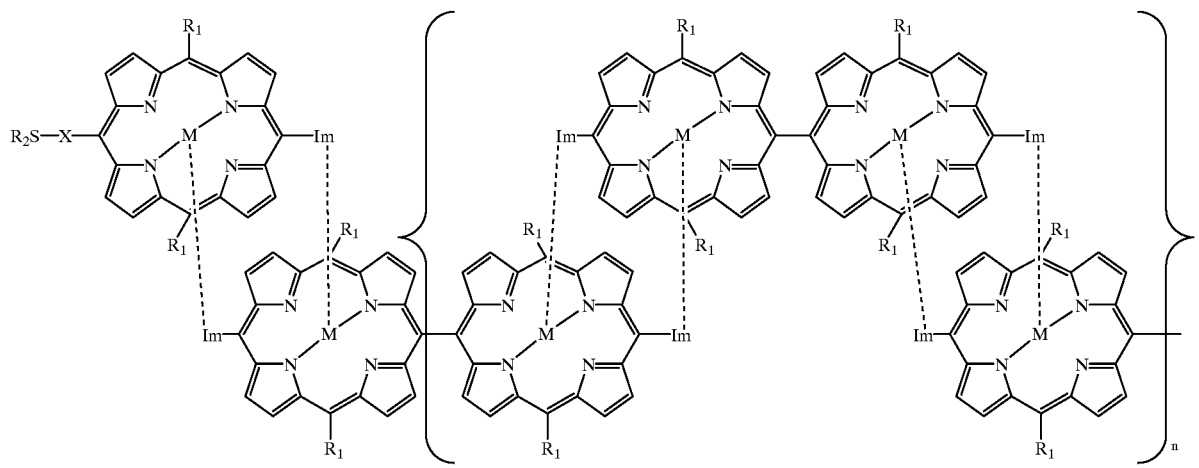

(4)

wherein each of $R_1$, M, $R_2$, X and Im including $R_3$ has the same meaning as defined in item (1) above; and n represents an integer of 0 or more.

(11) The poly(imidazolylporphyrin metal complex) represented by the general formula (4) according to item (10) above, wherein $R_1$ represents a group selected from the group consisting of an alkyl group having 3–20 carbon atoms, aryl group having 6–20 carbon atoms, alkyl-substituted aryl group having 7–24 carbon atoms and alkyloxy-substituted aryl group having 7–24 carbon atoms; X represents a divalent linking group containing at least one group selected from the group consisting of —$(CH_2)_n$— (wherein n represents an integer of 1–17) and an arylene group having 6–14 carbon atoms.

(12) The poly(imidazolylporphyrin metal complex) represented by the general formula (4) according to item (10) or (11) above, wherein $R_1$ is an alkyl group having 3–20 carbon atoms; M is Zn ion; X is a phenylene group; $R_2$ is an acetyl group; and Im is $Im_1$ (wherein $R_3$ is a methyl group).

(13) A method for preparing a porphyrin metal complex dimer represented by the general formula (2) mentioned in item (4) above, comprising steps of;

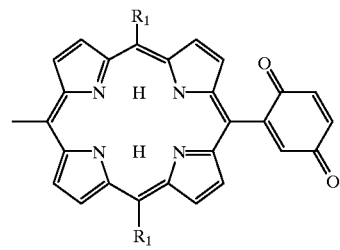

(i) reacting compounds-a to -c:

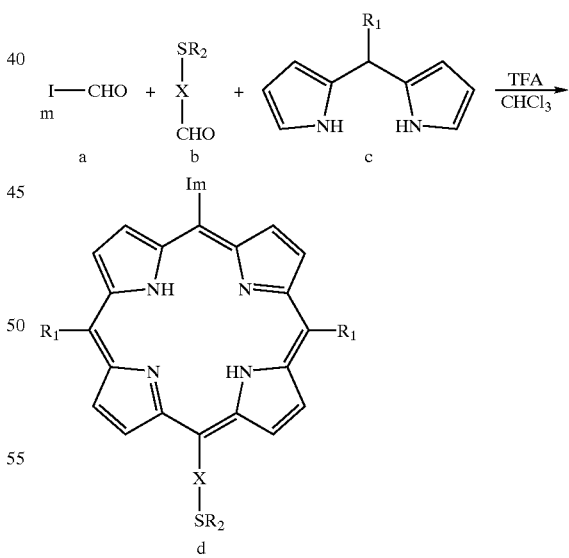

wherein each of Im including $R_3$, X, $R_1$ and $R_2$ has the same meaning as defined in item (1) above, with trifluoroacetic acid thereby obtaining a porphyrin of compound d (wherein each of Im including $R_3$, X, $R_1$ and $R_2$ has the same meaning as defined in item (1) above); and (ii) inserting a metal ion of M (wherein M has the same meaning as defined in item (1) above), into the porphyrin of compound d:

thereby obtaining the porphyrin metal complex dimer represented by the general formula (2), wherein the steps (i) and (ii) are performed in a solvent having low polarity.

(14) A method for preparing a porphyrin metal complex monomer represented by the general formula (1) mentioned in item (1) above, wherein the porphyrin metal complex dimer represented by the general formula (2) mentioned in item (4) above is dissolved in a solvent having high polarity.

(15) A method of preparing poly(imidazolylporphyrin metal complex) represented by the general formula (3) mentioned in item (7) above, comprising steps of;

(i) dissolving the porphyrin metal complex dimer represented by the general formula (2) mentioned in item (4) above and a poly(imidazolylporphyrin) represented by formula (e):

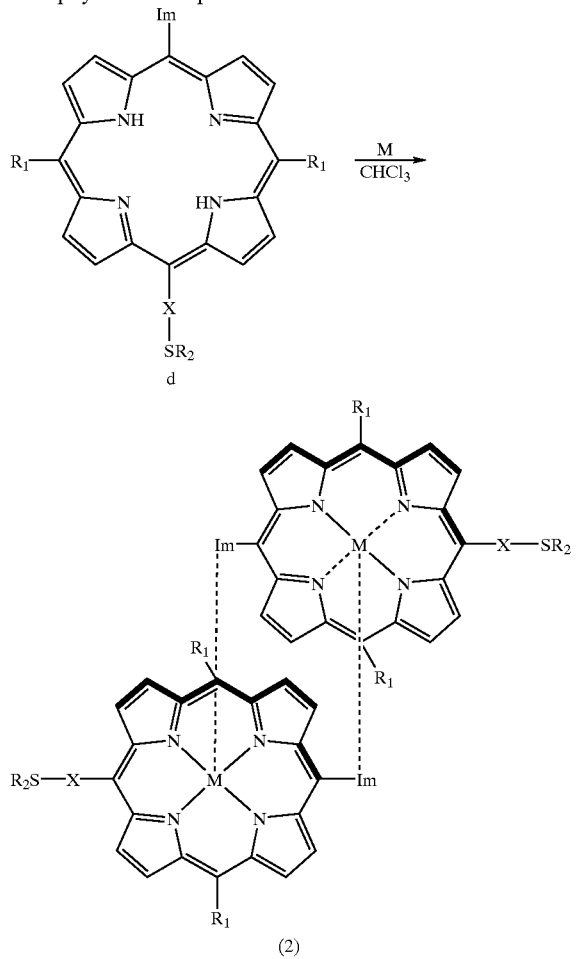

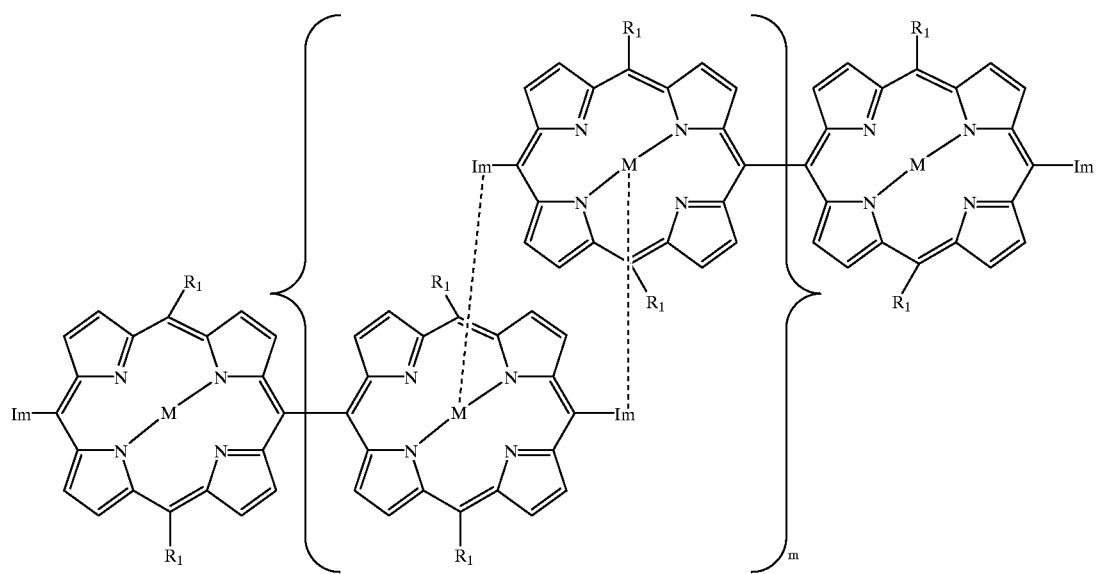

wherein each of $R_1$, Im including $R_3$, and M has the same meaning as defined in the general formula (1), and m represents an integer of 0 or more, in a solvent having high polarity; and then (ii) reducing the polarity of the solvent.

(16) A method of preparing the porphyrin represented by the general formula (4) mentioned in item (10) above, comprising a step of;

mixing a poly(imidazolylporphyrin) having a mercapto group at one end thereof, which is represented by a formula (f):

the group consisting of Zn(II), Ga(III), Fe(II), Co(II), and Ru(II). M is more preferably Zn (II) in view of manufacturability.

In the general formula (1), $R_1$ is a group selected from the group consisting of an alkyl group, unsubstituted aryl group, alkyl-substituted aryl group and alkyloxy-substituted aryl group. Although two $R_1$ present in the general formula (1) may be the same or different from each other, they are preferably the same in view of manufacturability.

Examples of the alkyl group represented by $R_1$ include straight chain alkyl groups, branched chain alkyl groups, and

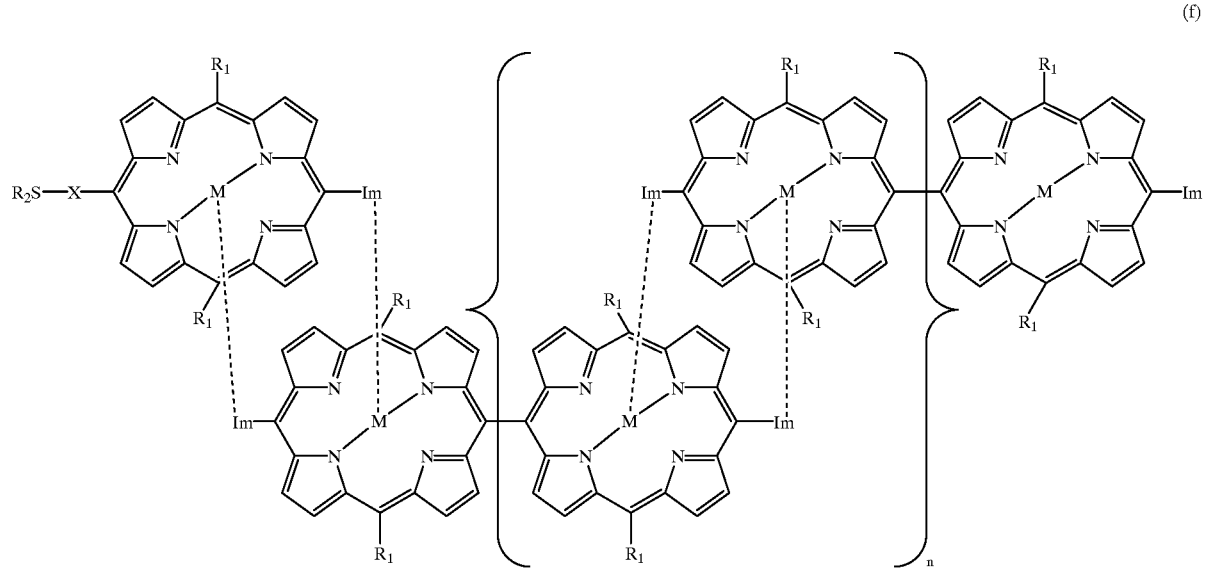

(f)

wherein each of $R_1$, $R_2$, Im including $R_3$ and M has the same meaning as defined in the general formula (1); and n is an integer of 0 or more, and a imidazolylporphyrin-quinonylporphyrin dimer represented by a formula (g):

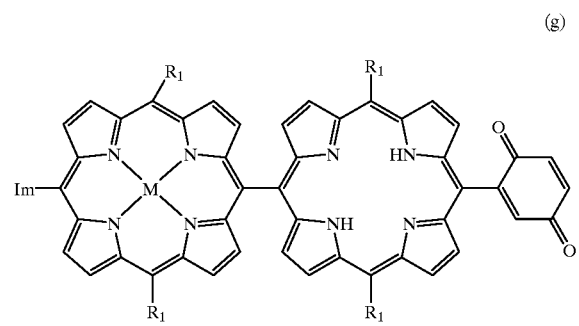

(g)

wherein each of $R_1$, Im including $R_3$, and M has the same meaning as defined in the general formula (1), in a solvent whose polarity is controlled.

Now, a mercapto-substituted imidazolylporphyrin metal complex monomer represented by the general formula (1) and polymers having the monomer as a constitutional unit and represented by general formulas (2)–(4) will be explained in detail.

In the general formula (1), an abbreviation M can be any metal ion as long as it can be employed as a central metal ion, but M preferably represents a metal ion selected from alicyclic groups. The number of carbon atoms of the alkyl group is preferably 3–20, more preferably 7–18. The alkyl group represented by $R_1$ may have at least one substituent as long as the substituent does not adversely affect the polymerization to become the poly(porphyrin) having the monomer of the general formula (1) as a constitutional unit, and as long as the polymer can transfer photonic energy and electronic energy.

Specific examples of the alkyl group represented by $R_1$ includes n-heptyl, n-nonyl, n-undecyl, and n-tridecyl.

Examples of the aryl group represented by $R_1$ include an aryl group having 6–20 carbon atoms, more preferably 6–12 carbon atoms. More specifically, the aryl group is phenyl, naphthyl, or biphenyl.

The aryl moieties of the alkyl-substituted aryl group represented by $R_1$ preferably include aryl groups having 6–14 carbon atoms, more preferably, 6–12 carbon atoms. Specific examples are phenyl, naphthyl, and biphenyl.

Examples of the alkyl group to be substituted on the aryl group of the alkyl-substituted aryl group include straight chain alkyl groups, branched chain alkyl groups, and alicyclic groups. The number of carbon atoms of the alkyl group is preferably 1–18, more preferably 1–12. The number of the alkyl substituent and the position thereof are not particularly limited as long as the number and the position thereof are a substitution-possible number and position on the aryl group, and do not adversely affect the polymerization of the porphyrin monomer represented by the general formula (1) into a poly(porhyrin), and the poly(porphyrin) thus polymerized is capable of transferring photonic energy and electronic energy. However, 1 to 3 alkyl groups may be substituted on the o-, m-, and/or p-positions in view of manufacturability and solubility etc. Of them, the substitution of the o-position is preferable since an undesirable side reaction can be suppressed.

Specific examples of the alkyl-substituted aryl group represented by $R_1$ include 4-methylphenyl, 4-octylphenyl, and 2,4,6-trimethylphenyl.

In the alkyloxy-substituted aryl group represented by $R_1$, the aryl moiety is the same as defined in the case of the alkyl-substituted aryl group.

Examples of the alkyloxy group to be substituted on the aryl group of the alkyloxy-substituted aryl group include straight chain alkyloxy groups, branched chain alkyloxy groups, and alicyclic oxy groups. The number of the alkyloxy substituent and the position thereof are not particularly limited as long as the number and the position thereof are a substitution—possible number and position on the aryl group, and do not adversely affect the polymerization of the porphyrin monomer represented by the general formula (1) into a poly(porhyrin), and the poly(porphyrin) thus polymerized is capable of transferring photonic energy and electronic energy. However, 1 to 3 alkyloxy groups may be substituted on the o-, m-, and/or p-positions in view of manufacturability and solubility etc. Of them, the substitution of the o-position is preferable since an undesirable side reaction can be prevented.

Specific examples of the alkyloxy-substituted aryl group represented by $R_1$ are 4-methoxyphenyl, 4-octyloxyphenyl, and 4-dodecyloxyphenyl.

In the general formula (1), X represents a divalent linking group containing at least one group selected from the group consisting of an arylene group and an alkylene group.

The term used to define X of "divalent linking group containing at least one group selected from the group consisting of an arylene group and an alkylene group" includes a group selected from the groups consisting of -(alkylene)-, -(arylene)-, -(alkylene)-(arylene)-, and -(arylene)-(alkylene)-.

The alkylene group represented by X includes —$(CH_2)_n$—, wherein n is an integer of 1 to 17, preferably 1 to 13.

The arylene group represented by X preferably represents a divalent group obtained by eliminating a single hydrogen atom from the aryl group represented by $R_1$, more preferably, a phenylene group. The two linking positions of the phenylene group are not particularly limited, but are preferably m- and p-positions.

X is preferably a phenylene group in view of manufactuability.

In the general formula (1), $R_2$ represents a hydrogen atom or an acetyl group.

In the general formula (1), the imidazolyl group of Im is represented by $Im_1$ or $Im_2$ set forth below:

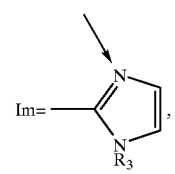

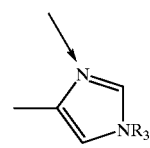

In the formulas $Im_1$ and $Im_2$, $R_3$ represents a hydrogen atom or an alkyl group.

The alkyl group represented by $R_3$ includes straight chain alkyl groups, branched chain alkyl groups, and alicyclic alkyl groups. The number of carbon atoms of the alkyl group represented by $R_3$ is not particularly limited as long as polymerization of porphyrin monomer represented by the general formula (1) is not adversely affected, and as long as the poly(porphyrin) thus polymerized is capable of transferring photonic energy and electronic energy. However, $R_3$ preferably has 1–4 carbon atoms. More preferably, $R_3$ is a methyl group when manufacturability is taken into consideration.

In the mercapto-substituted imidazolylporphyrin metal complex dimer (hereinafter, sometimes referred to as "complementarily coordinated dimer") represented by the general formula (2) of the present invention, $R_1$, M, X, $R_2$, Im and $R_3$ are the same as defined in the case of $R_1$, M, X, $R_2$, Im and $R_3$ of the general formula (1), respectively.

The imidazol ring and the benzene ring represented by $R_1$ and X to be connected to the complementarily coordinated dimer of the general formula (2) are individually arranged and extended over a plane substantially in perpendicular to the plane formed of the pyrrole rings linked by methine groups.

In the complementarily coordinated dimer of the general formula (2), the central metal ion M is bonded to a nitrogen atom of the pyrrole ring by coordination bonding. The central metal ion M is also bonded to imidazolyl group (Im) by coordination bonding. They are bonded at coordination sites indicated by arrows in $Im_1$ and $Im_2$ mentioned above.

The coordination bonding between the central metal ion M and Im is very strong. For example, a literature (Bull. Chem. Soc. Jap. 69, 3563 (1996)) discloses that the coordination bonding between the nitrogen atom of an imidazolyl group and a porphyrin complex (which have a similar structure to that of the porphyrin complex constructing the dimer of the general formula (2) of the present invention) can be maintained even at a concentration of $10^{-9}$M.

Although two porphyrin monomers constructing the complementarily coordinated dimer of the general formula (2) may be the same or different from each other, they are preferably the same in view of manufacturability.

In the imidazolylporphyrin metal complex dimer having a mercapto group at both ends thereof, and represented by the general formula (3) of the present invention, $R_1$, $R_2$, M, Im (including $R_3$) are the same as defined for $R_1$, $R_2$, M, Im (including $R_3$) of the general formula (1), respectively, and n is an integer of 0 or more.

The value of n of the general formula (3) may be appropriately set depending upon use of the poly (imidazolylporphyrin metal complex) having the mercapto group at both ends and thus not particularly limited. For example, when the poly(imidazolylporphyrin metal complex) is used in a photonic energy transferring device having an array with a length of tens to hundreds nanometer, n can be set at up to about 714 based on the calculation under the assumption that the repeating unit has a length of 1.4 nm. If a longer poly(porphyrin) array over the tens to hundreds nanometer is desired, the value n can be further increased to, for example, about 800 to 1000. At present, the present inventors have succeeded in synthesizing a poly(imidazolyl porphyrin metal complex) having the value n of up to about 400 and the mercapto group at both ends.

The poly(imidazolyl porphyrin metal complex) having a mercapto group at both ends (represented by the general formula (3)) has the following dimer as a constitutional unit. The dimer unit is formed of two porphyrin monomers (each having an imidazolyl substituent) are connected directly to each other, in such a way that π-orbital planes, which is formed of four pyrrole nuclei, are arranged in an orthogonal orientation as set forth below (hereinafter this dimer unit is referred to as a "meso—meso dimer").

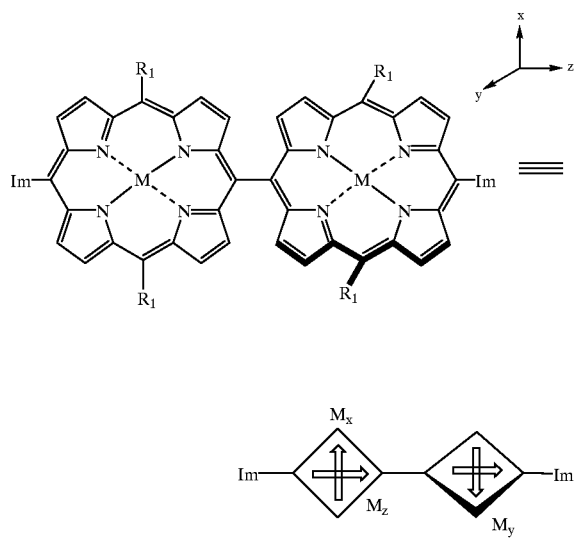

In poly(imidazolyl porphyrin metal complex) represented by the general formula (3), the three-dimensional structure of the meso—meso dimer is maintained as it is. These meso—meso dimers are formed into an array in such a way that one of the π-planes of one meso—meso dimer faces to one of the planes of another meso—meso dimer in alternative way.

The corresponding substituents (M, $R_1$, and Im (including $R_3$)) of two monomers constructing the meso—meso dimer may be the same or different from each other. However, they are preferably the same in view of manufacturability and purification. Furthermore, although the corresponding substituents (M, $R_1$, and Im including $R_3$) of a plurality of meso—meso dimers constituting the poly (imidazolylporphyrin metal complex) represented by the general formula (3) may be the same or different from each other, they are preferably the same if the manufacturability is taken into consideration. Furthermore, although the two $R_2S$—X— groups that attach to one end and the other end, respectively, may be the same or different from each other, they are preferably the same in view of manufacturability.

In the poly(imidazolyl porphyrin metal complex) represented by the general formula (3), the coordinate bond between the central metal ion M and the imidazolyl group (Im) can be cleaved by controlling the polarity of a solvent dissolving the polymer. To describe more specific, when the polarity of the solvent is increased by adding a polar solvent such as methanol, ethanol, or pyridine, the coordinate bonding between the central metal ion M and the imidazolyl group (Im) is likely to be cleaved, with the result that the value n of the general formula (3) decreases. For example, the poly(imidazolyl porphyrin metal complex) of the general formula (3) is dissolved in a polar solvent that is free from a non-polar solvent, the value n decreases. Conversely, when the polarity of the solvent is decreased, the coordinate bonding between the central metal ion M and the imidazolyl group (Im) is reconstructed, with the result that the value n of the general formula (3) increases. For example, the poly(imidazolyl porphyrin metal complex) or the general formula (3) is dissolved in a non-polar solvent that is free from a polar solvent, the value n increases. As the solvent for decreasing the polarity, chloroform, benzene, toluene and the like may be used.

The value n of the general formula (3) varies depending upon various factors such as types of porphyrin rings including an imidazolyl group, the molecular structure and concentration of the solvent, other than the polarity of the solvent. One skilled in the art can set the value of n of the general formula (3) at a desired value by appropriately setting the polarity of a solvent in view of these factors.

Now, the connection between the poly (imidazolylporphyrin)metal complex represented by formulas (3) or (4) of the present invention and an electrode will be explained below. It is known that when a gold electrode is only dipped in a solution containing the compound having an acetylthiophenyl group, the acetyl group is dissociated from the compound to produce a strong Au—S bond. As a result, a single molecular layer is formed on the surface of the gold electrode in a self-organized manner.

Therefore, of the poly(imidazolyl porphyrin metal complex) of the general formula (3) having a mercapto group at both ends, the complex having an acetyl—S—X— group at the ends may be used to form an electric wire for connecting between gold electrodes by dipping the gold electrodes in a solution having this compound dissolved in a non-polar solvent such as chloroform, as shown below:

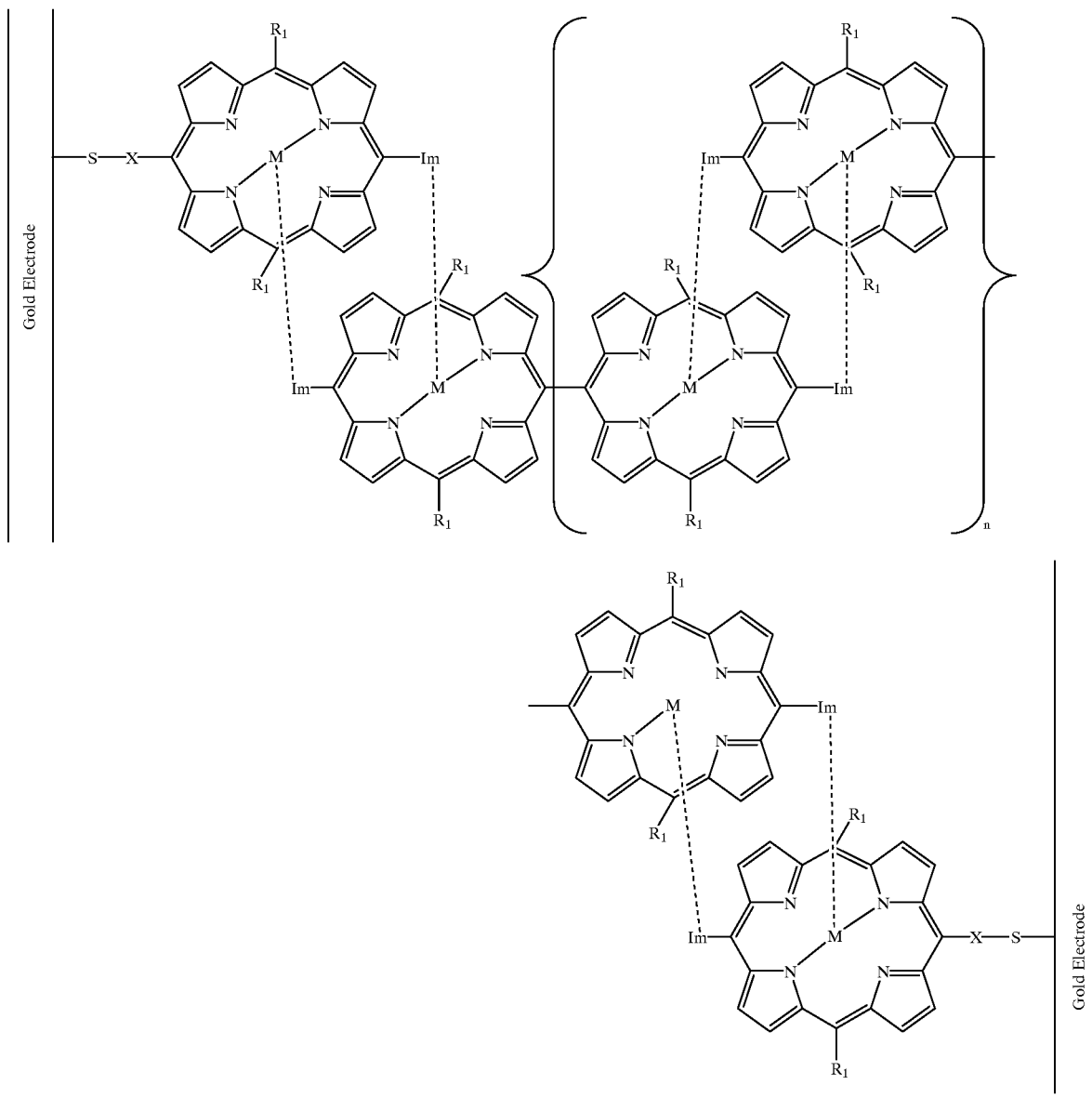

(3)

The poly(imidazolylporphyrin metal complex) represented by the general formula (4), which has a mercapto group at one end and a quinonyl group at the other end, is the same as the polymer represented by the general formula (3), except that the $R_2S$—$X$— group at one end of the polymer of formula (3) is substituted by a p-benzoquinonyl group and that the central metal ion M of the porphyrin ring bound to the p-benzoquinonyl group is deleted.

In the poly(imidazolylporphyrin metal complex) of the general formula (4) the closest distance between central metal ions within the meso—meso dimer unit (hereinafter referred to as "intra-dimer distance") is 0.84 nm. The closest distance between the central metal ion of one meso—meso dimer and the central metal ion of another meso—meso dimer (hereinafter referred to as "inter-dimer distance") is 0.59 nm, as estimated on the basis of the description of Cerius (Angew. Chem, Int. Ed. Engl. 33, 655–657 (1994)).

As described above, the poly(imidazolylporphyrin metal complex) of the general formula (4) having the above mentioned "intra-dimer distance" and "inter-dimer distance", is equal to a closely spaced chlorophylls of a natural-occurring antenna ring. For example, it is said that the "intra-dimer distance" and the "inter-dimer distance" of B850 derived from *Phodopseudomonas acidophilia* are 0.95 nm and 0.89 nm, respectively. By arranging chlorophylls in such a short distance, a strong mutual excitation interaction of chromophores is induced, and the resulting excitation delocalization on the pigment is the source of ultra-fast excitation dynamics. Based on this phenomenon, it is strongly implied that the poly(imidazolylporphyrin metal complex) having a mercapto group at one end and a quinonyl group at the other end may realize an energy transport system.

More specifically, if the SX-group at one end of the compound of the general formula (4) is bonded to a gold electrode as shown in the following formula, it is possible to construct the energy/electron transport system consisting of an antenna complex→special pair→pheophytin→quinone, thereby constructing an artificial photosynthesis system.

is a zinc ion and $R_2$ is an acetyl group. However, the method is not limited to this. In addition, the complementarily coordinated dimers of the general formula (2) having other substituents may be prepared by one skilled in the art by appropriately setting reaction conditions such as compounds, catalysts, and reaction temperatures.

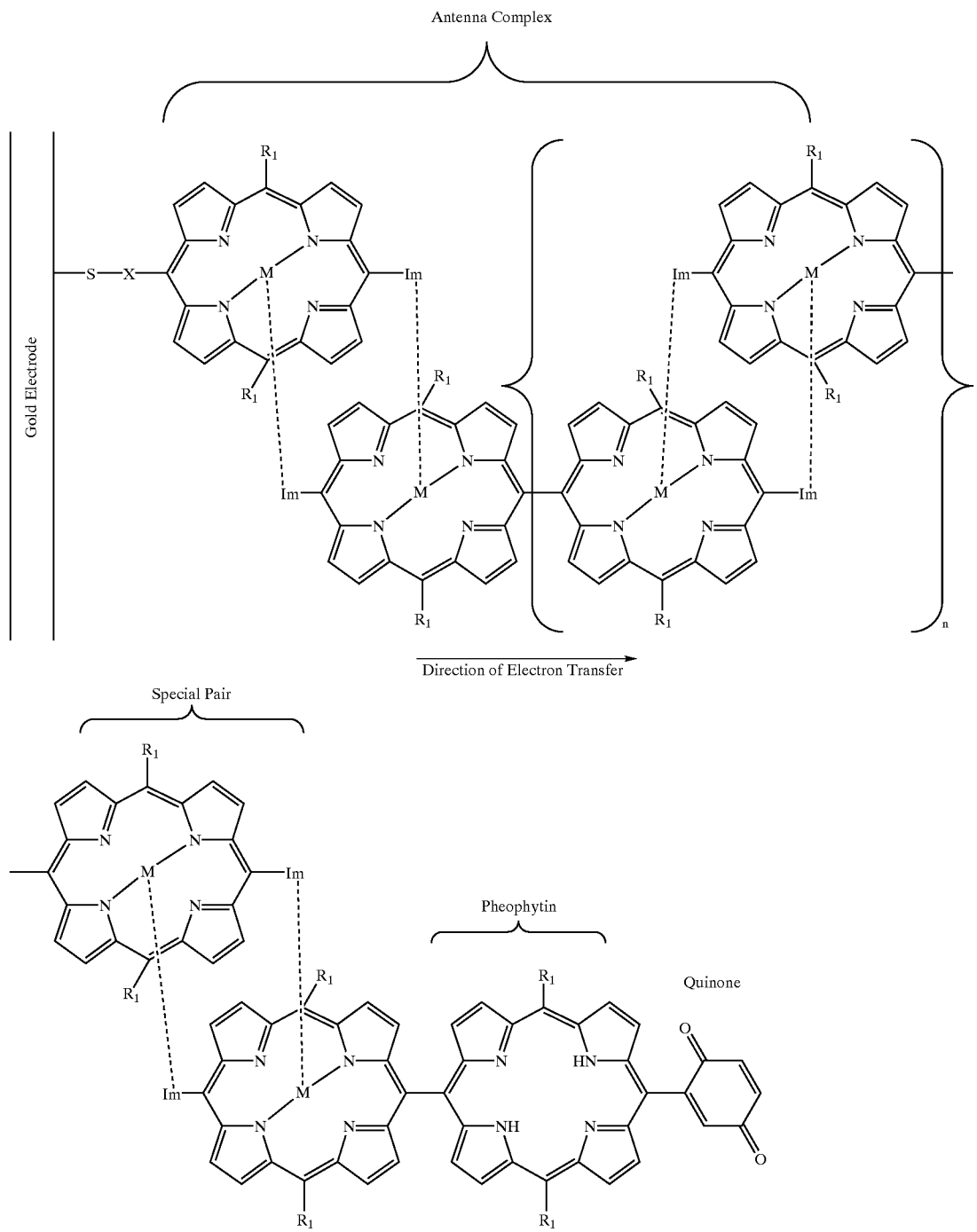

Now, we will explain the method of synthesizing a mercapto-substituted imidazolylporphyrin metal complex dimer (complementarily coordinated dimer) represented by the general formula (2), by referring to a dimer wherein M

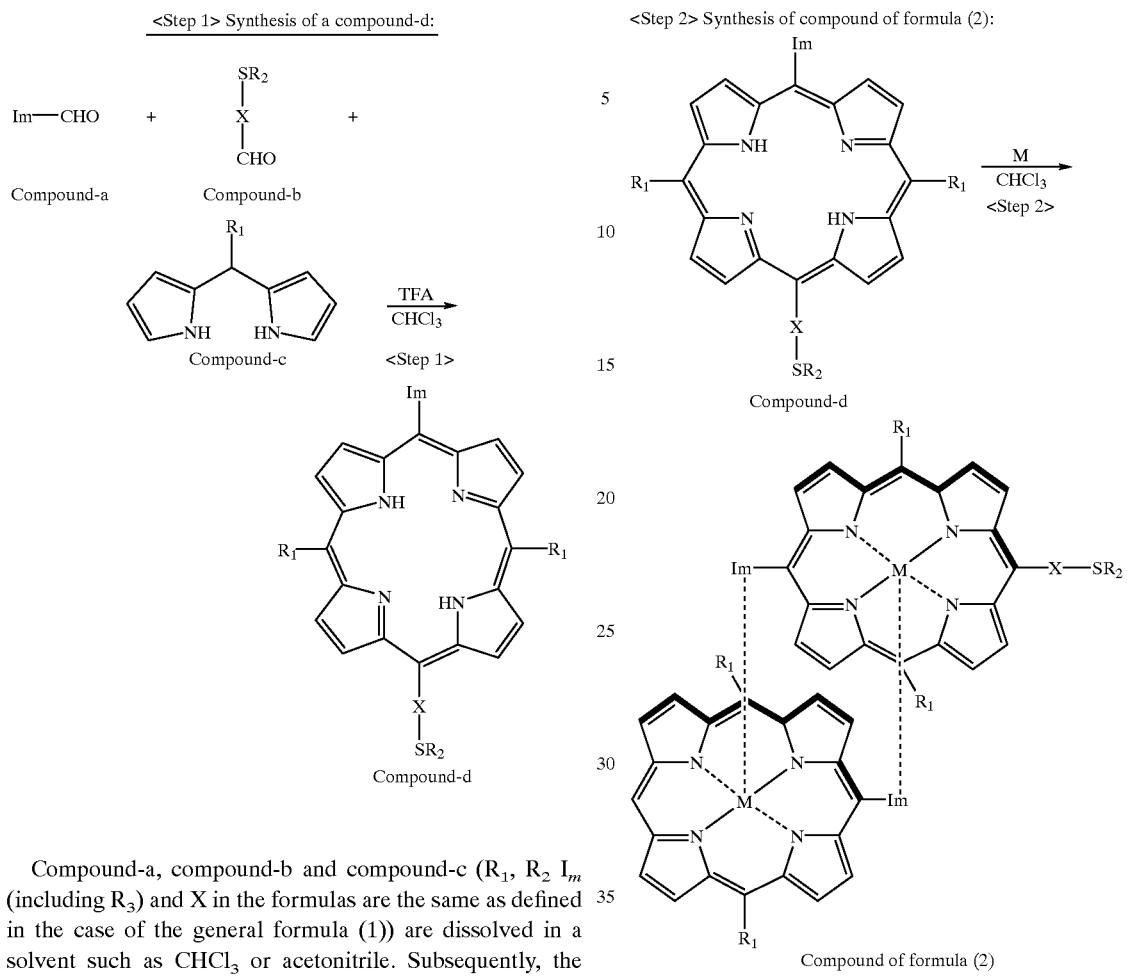

Compound-a, compound-b and compound-c ($R_1$, $R_2$ $I_m$ (including $R_3$) and X in the formulas are the same as defined in the case of the general formula (1)) are dissolved in a solvent such as $CHCl_3$ or acetonitrile. Subsequently, the atmosphere of the mixture is substituted to a nitrogen atmosphere. To the resultant mixture, TFA (trifluoroacetic acid) is added and allowed to react them to synthesize a porphyrin of compound-d. Compounds-a, -b, and -c are commercially available or obtained by known methods disclosed in documents.

The addition ratio in amount of compounds-a, -b, and -c is generally set at 1:1:2.

The volume of the solvent is generally 500–1000 times the weight of compound-b.

The reaction temperature is generally set at 20–30° C. The reaction time is generally set at 1–3 hours.

The substance obtained from the aforementioned reaction, subjected to a purification step or the like, if necessary, and then subjected to the following step 2. The purification step before step 2 can be performed as follows: After the solvent used in the aforementioned reaction is removed by distillation, the resultant substance is dissolved in a solvent such as chloroform or dichloromethane. An aqueous solution of sodium bicarbonate is further added to the solution and fractionated. After an organic layer is concentrated to dryness, the resultant solution is subjected to silica gel column chromatography or the like.

The compound-d obtained in the step 1 is converted into a zinc complex of formula (2). The reaction is performed by dissolving the compound-d in a solvent such as chloroform or dichloromethane and adding a zinc salt (e.g., zinc(II) acetate, zinc(II) chloride) to the solution.

The addition amount of the zinc salt may be generally set at 5–20 times the weight of the compound-d.

The reaction temperature may be generally set at room temperature of about 25–30° C. The reaction time may be generally set at 1–3 hours.

After the reaction, the reaction solution is washed with distilled water and the organic layer is concentrated under reduced pressure. As a result, the dimer ($R_2$ is an acetyl group) of the general formula (2) is obtained.

The compound of the general formula (2) where $R_2$ is a hydrogen atom, may be synthesized by hydrolyzing the compound-e obtained by the aforementioned method. The hydrolysis is performed, for example, by dissolving the compound-e in a solvent such as chloroform or dichloromethane and adding 1N hydrochloric acid thereto. The reaction temperature is generally set at room temperature (25–30° C.). The reaction time is set at 10–20 minutes. The addition amount of the hydrochloric acid is 20–50 times the weight of the compound-e.

The mercapto-substituted imidazolylporphyrin metal complex monomer of the general formula (1) is prepared as follows: The complementarily coordinated dimer of the general formula (2) is dissolved in a high polar solvent to cleave the coordinate bond between the central metal ion and a nitrogen atom of the imidazolyl group. The high polar solvent may be a polar solvent free from a non-polar solvent. However, in some cases where $R_1$ in the general formula (2) has low polarity, the high polar solvent must be a mixture of solvents of a polar solvent and a non-polar solvent, in order to dissolve the dimer. The high polar solvent include methanol, ethanol and the like.

The poly(imidazolylporphyrin metal complex) having a mercapto group at both ends of the general formula (3) is produced by dissolving the mercapto-substituted imidazolylporphyrin metal complex dimer of the general formula (2) and the poly(imidazolylporphyrin) of the formula (e) in a high-polar solvent, and then decreasing the polarity of the solvent, for example by replacing at least a part of the solvent with a non-polar solvent.

The poly(imidazolylporphyrin) of the formula (e) employed herein can be synthesized by the following steps (a)–(c).

Step (a): A metal ion M is inserted into the porphyrin monomer of a formula (II) as the central metal ion of the porphyrin. As a result, the complementarily coordinated dimer represented by a formula (III) is obtained, as set forth below:

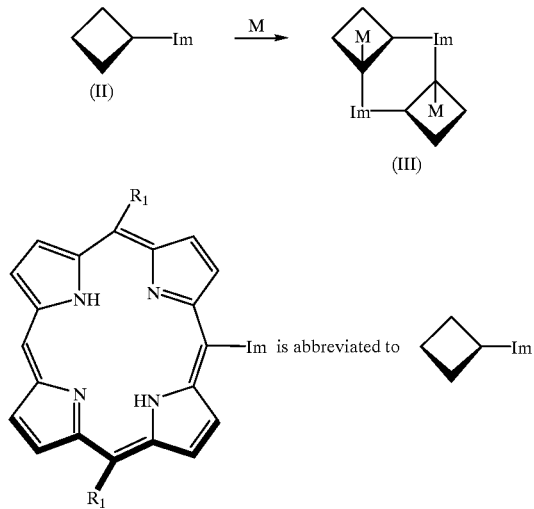

Where M, $R_1$ and Im (including $R_3$) are the same as defined in the case of the general formula (I).

Step (b): A coupling reaction between the monomer unit of the complementarily coordinated dimer of the formula (III) obtained in the step (a), is performed thereby forming another dimer of meso-type, in which each of the monomer units are bonded at meso position thereof. Then, the central metal ions are removed from the thus obtained meso—meso dimer, thereby obtaining the dimer represented by formula (IV):

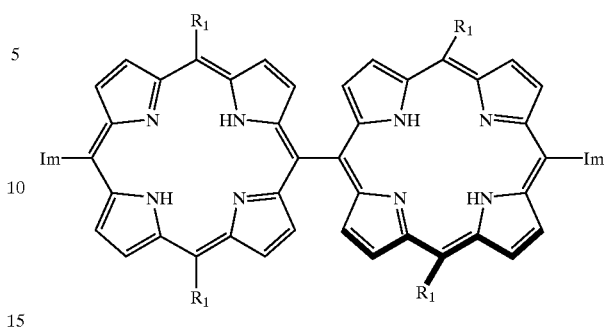

Where $R_1$ and Im (including $R_3$) are the same as defined in the case of the general formula (I).

Step (c): A central metal ion M is inserted in the meso—meso dimer of the general formula (IV) obtained in the step (b) to coordinate the central metal to Im. As a result, the poly(porphyrin) of the formula (e) is obtained.

Now, the method of producing the poly(porphyrin) represented by the formula (e) of the present invention will be explained by referring to a poly(porphyrin), wherein $R_1$=n-$C_7H_{15}$, M=Zn, and Im=$Im_1$ ($R_2$=methyl group) as an example. However, the method of producing the poly (porphyrin) of the formula (e) is not limited to this example. In addition, it is possible for one of ordinary skill in the art to produce other poly(porphyrin) within the scope of the formula (e) by appropriately varying a compound(s) to be used and reaction conditions such as a catalyst and a reaction temperature.

The starting material of the step (a), that is, a porphyrin monomer represented by a general formula (II) is obtained by dissolving 1-methylimidazole-2-carboxyaldehyde, formaldehyde, and meso-(n-heptyl)dipyrromethane in a nonpolar solvent, stirring the mixture, and thereafter, adding trifluoroacetic acid and dichlorodicyano-p-benzoquinone to the resultant mixture.

In the aforementioned reaction, 1-methylimidazole-2-carboxyaldehyde and formaldehyde are commercially available. Meso-(n-heptyl) dipyrromethane may be produced from octanal and pyrrole in accordance with a method described in technical literatures.

A mole ratio of 1-methylimidazole-2-carboxyaldehyde: formaldehyde: meso-(n-heptyl)dipyrromethane generally falls within the range of 1:4:2 to 1:3:2.

As the nonpolar solvent, chloroform, THF or the like may be used. Generally, the nonpolar solvent is used in an amount that is 500–1000 times the weight of chemical compounds to be reacted.

The amount of trifluoroacetic acid to be added to the reaction solution is generally 1 to 3 times that of 1-methylimidazole-2-carboxyaldehyde, in terms of mole. This reaction of these compounds are generally performed at a temperature near room temperature under an inert gas atmosphere such as nitrogen while stirring for 20 to 40 minutes.

The amount of dichlorodicyano-p-benzoquinone to be added to the reaction solution after stirring is 2 to 4 times that of 1-methylimidazole-2-carboxyaldehyde, in terms of mole. This reaction is generally performed with stirring for 30 minutes to one hour.

The resultant reaction solution is washed with an aqueous solvent such as aqueous sodium bicarbonate, and thereafter, an organic layer is evaporated. In this manner, a crude product represented by the general formula (II) can be obtained. The crude product is, if necessary, purified by means of column chromatography or the like, and then used as the starting material of the step (a).

In the step (a), the porphyrin monomer represented by the general formula (II) is dissolved in a nonpolar solvent and a solution containing a zinc salt dissolved in an organic solvent is added to the above-prepared solution. In this manner, a complementarily coordinated dimer represented by the general formula (III) can be obtained.

As an example of the nonpolar solvent for dissolving the porphyrin monomer of the general formula (II), chloroform, or dichloromethane may be used. Generally, the amount of the nonpolar solvent may be 100 to 200 times of the weight of the compound to be dissolved.

As the solution prepared by dissolving a zinc salt in an organic solvent, a solution prepared by dissolving, zinc acetate, zinc chloride, or the like in an organic solvent such as methanol or ethanol may be used. The molar amount of the zinc salt is 5 to 20 times that of the monomer represented by the general formula (II) in terms of zinc.

The reaction mixture is generally stirred for 1 to 3 hours at around room temperature. After the resultant reaction solution is washed with an aqueous solvent such as water, the organic layer is removed by evaporation. As a result, a crude product of the complementarily coordinated dimer represented by the general formula (III) can be obtained.

In the step (b), the complementarily coordinated dimer represented by the general formula (III) and iodine are dissolved in a nonpolar solvent. After silver(I) hexafluorophosphate dissolved in an organic solvent is added and stirred, iodine and silver(I)hexafluorophosphate are further added to the reaction mixture and stirred. Through this reaction, another type of dimer constructed with the monomer units each of which is originated from the complementarily coordinated dimers represented by the general formula (III) and which are bonded at meso-position thereof to each other, is formed. Then, the resultant solution is washed with an aqueous solvent and concentrated to dryness.

Subsequently, the residue is dissolved in an acid-containing organic solvent and stirred, thereby the central metal ions are removed. After an aqueous solvent is added, the resultant solution mixture is subjected to extraction with an organic solvent. As a result, a crude product of the meso—meso dimer represented by the general formula (IV) is obtained.

As the nonpolar solvent for dissolving the complementarily coordinated dimer represented by the general formula (III), chloroform or the like is used in an amount which is 500 to 1000 times the weight of the chemical compound to be reacted. Iodine and silver(I)hexafluorophosphate may be added in an amount 0.4 to 0.6 times that of the dimer represented by the general formula (III) in terms of mole, for each.

As an example of the organic solvent for dissolving silver(I)hexafluorophosphate, acetonitrile, or acetone may be added in an amount 100 to 200 times the weight of silver(I)hexafluorophosphate.

The stirring is generally performed at room temperature for 1 to 3 hours.

The amounts of iodine and silver(I)hexafluorophosphate to be further added are 0.4 to 0.6 times that of the dimer of the general formula (III), for each. The reaction solution is generally stirred for 1 to 3 hours.

As an example of the aqueous solvent for washing the reaction solution, an aqueous sodium bicarbonate solution, or water may be used.

As the acid-containing organic solvent for dissolving the residue after washing, any organic solvent may be used as long as it can reduce a pH value of the reaction mixture to 1 or less. For example, methanol/conc. hydrochloric acid (10:1) mixture may be used in an amount 200 to 500 times the weight of the chemical compounds to be reacted in the coupling reaction. The reaction solution is generally stirred at room temperature for 20 to 40 minutes.

As an example of the aqueous solvent to be added to the resultant reaction solution, water may be used. As an example of the organic solvent for use in extraction, chloroform may be used.

The crude product of the meso—meso dimer of the general formula (IV) thus obtained, if necessary, is washed with an aqueous solvent such as aqueous sodium bicarbonate or water, and purified by chromatography or the like and thereafter, subjected to the next step (c).

In the step (c), the meso—meso dimer of the general formula (IV) is dissolved in a solvent having low polarity. To the resultant solution, a zinc salt dissolved in an organic solvent is added and stirred. As a result, the poly(porphyrin) represented by the formula (e) can be obtained.

As mentioned above, the degree of polymerization varies depending on the polarity of the solvent that is used in the step (c). One of ordinary skill in the art can set the degree of the polarity of the solvent depending on many factors including the chemical structure of the porphyrin ring including substituents that attach to the porphyrin ring, such as $R_1$ and Im, chemical structure of the solvent and the concentration thereof. When the reaction in the step (c) is performed in a solvent free from a polar solvent, i.e., in a non polar solvent, the degree of polymerization can reach maximum.

As an example of the nonpolar solvent to be used in the reaction of the step (c), chloroform, or dichloromethane may be used. The nonpolar solvent may be used in an amount that is 100 to 200 times the weight of the compound.

As the solution having a zinc salt dissolved in an organic solvent and to be added to the reaction mixture, use is made, for example, of a saturated solution containing zinc acetate, or zinc chloride dissolved in an organic solvent such as methanol or ethanol. The molar amount of the zinc salt may be 5 to 20 times that of the meso—meso dimer of the general formula (IV) in terms of zinc.

The reaction is generally performed at room temperature for 1 to 3 hours with stirring, thereby poly(porphyrin) represented by the formula (e) of the present invention can be obtained.

The reaction of the porphyrin metal complex represented by the general formula (2) with the poly(porphyrin) of the formula (e) to obtain the poly(imidazolylporphyrin metal complex) having a mercapto group at both ends (general formula (3)) is as follows: The porphyrin metal complex is mixed with the poly(porphyrin) in the presence of a high polar solvent such as methanol. Thereafter the polarity of the reaction mixture is reduced by, for example, adding a non-polar solvent such as chloroform.

In the aforementioned reaction, the polarity of the solvent, more specifically, the ratio in amount of the polar solvent and non-polar solvent can be appropriately set depending upon the polymerization degree of the poly(porphyrin) of the formula (e) and a desired value of n of the general formula (3). The value of n of the general formula (3) can be maximized by using a non-polar solvent in which polar solvent is not contained. The reaction temperature is generally set at 20–30° C. and the reaction time is generally set at 5–10 minutes.

The poly(imidazolylporphyrin metal complex) represented by the general formula (4) can be synthesized by mixing the mercapto-substituted poly(imidazolylporphyrin metal complex)-imidazolyl (the formula (f)) and the imidazolylporphyrin-quinonyl porphyrin dimer (the formula (g)) under a condition in which polarity of the solvent is controlled. Specifically, when the reaction is conducted in a non-polar solvent free from a polar solvent, n in the formula (f) can be maximized.

The poly(imidazolylporphyrin metal complex) represented by the formula (f) can be produced by the following method.

First, the imidazolylporphyrin metal complex dimer of the general formula (2) is bonded to the surface of a gold electrode in a solvent having high polarity, thereby forming a gold electrode modified with the imidazolylporphyrin metal complex. Then, the poly(porphyrin) of the above mentioned formula (e) is reacted with the gold electrode modified with the imidazolylporphyrin metal in a solvent having high polarity. As a result, a desired poly (imidazolylporphyrin metal complex) imidazolyl having a mercapto group at one of both ends, as shown in the formula (f).

On the other hand, the imidazolylporphrin-quinonylporphrin dimer of the formula (g) is synthesized by the following steps 3 to 13.

Synthesis Route

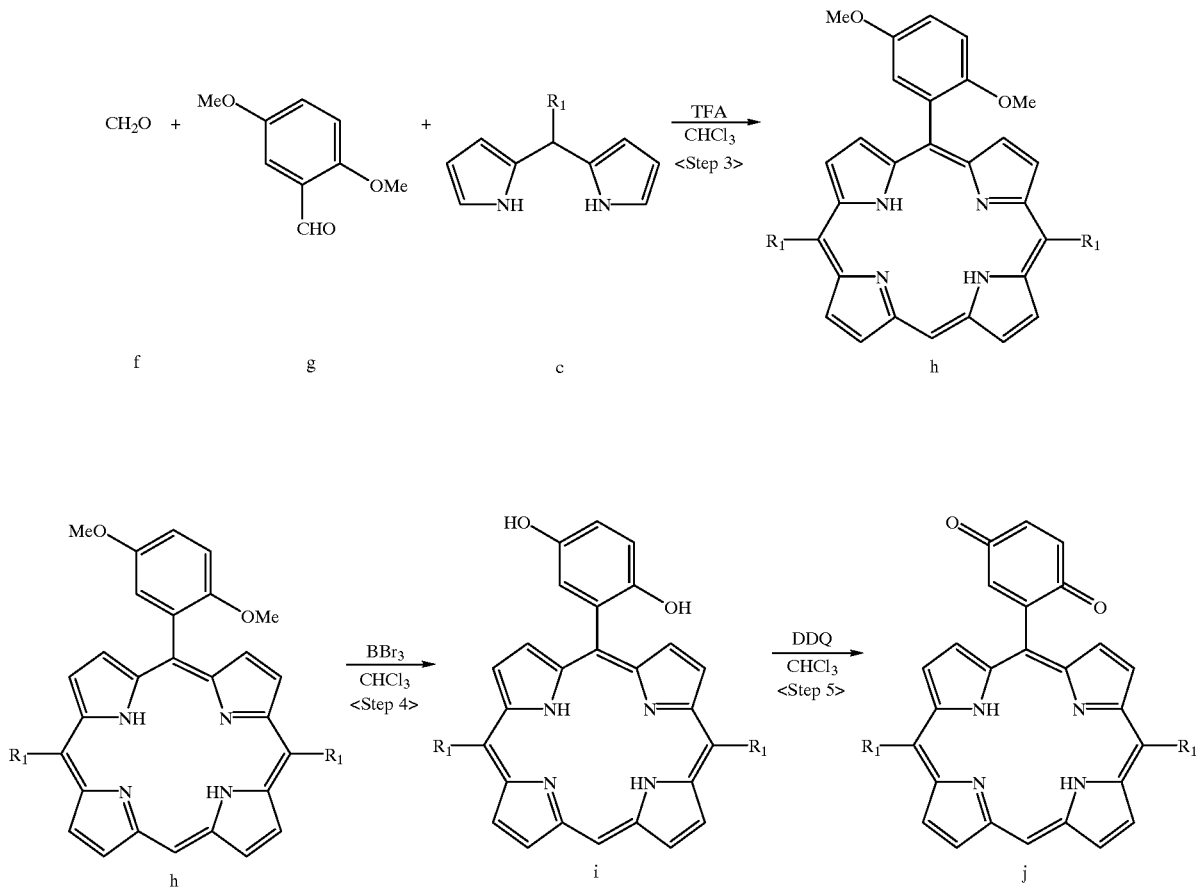

-continued
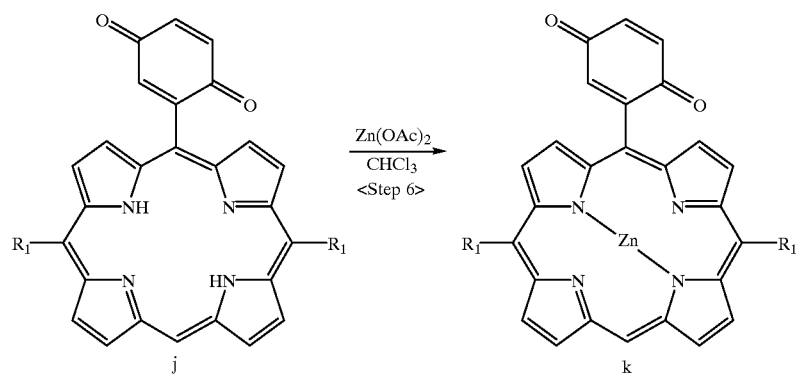
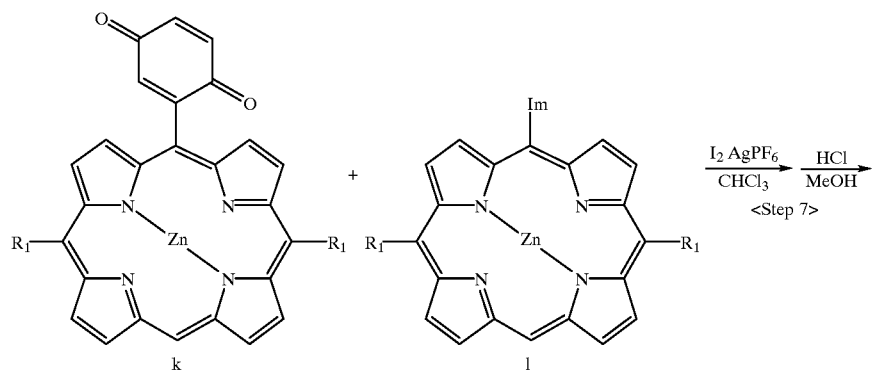
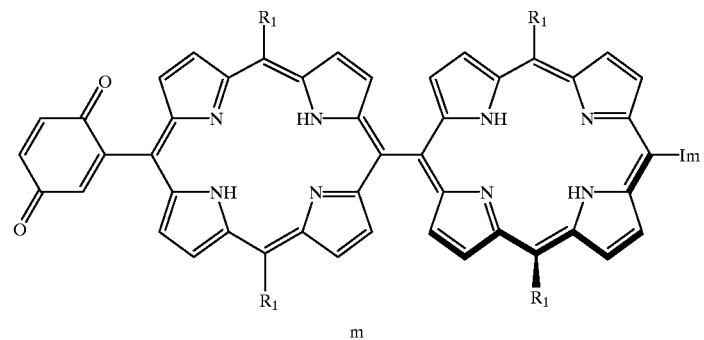
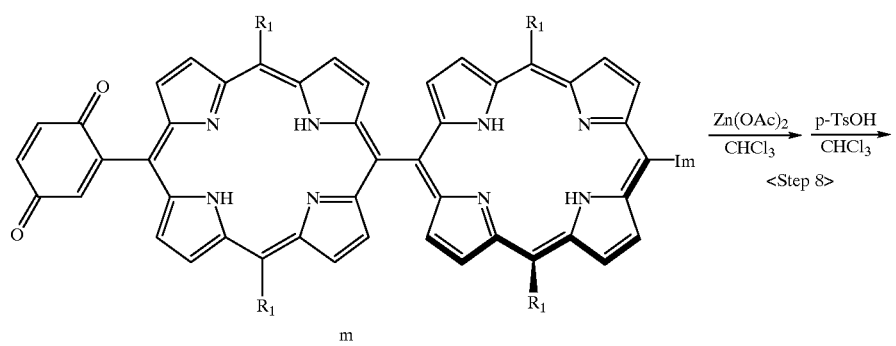

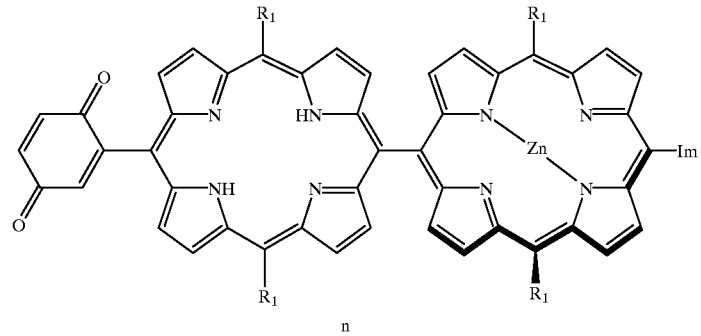

<Step 3> Synthesis of a compound-h

A compound-f, compound-g and compound-c (where $R_1$ is defined above) are dissolved in a solvent such as $CHCl_3$ or acetonitrile, and the atmosphere of the mixture is substitution with nitrogen. After TFA (trifluoroacetic acid) is added to the reaction solution and allowed to react with the solution to synthesize porphyrin of compound-h. Commercially available products are used as compounds-f, -g, and -c.

The addition ratio of the compounds-f, -g and -c to be added may generally set at 1:1:2.

The solvent is generally used in an amount of 500–1000 times the weight of the compound-b.

The reaction temperature is generally set at 20–30° C. The reaction time is generally set at 1 to 1.5 hours.

The substance obtained from the aforementioned reaction is subjected to a purification step, if necessary, and then subjected to the step 4. The purification step is performed as follows. After the solvent used in the aforementioned reaction is removed by distillation, the resultant material is dissolved in a solvent such as chloroform or dichlormethane. To the resultant solution, an aqueous solution of sodium bicarbonate is added. After the solution is fractionated, the organic layer is concentrated to dryness and subjected to silica gel column chromatography or the like.

<Step 4> Synthesis of compound-i

The compound-h obtained in the step 3 is dissolved in a solvent such as $CHCl_3$ or benzene. Thereafter, boron tribromide is added to the resultant solution and allowed to react them to synthesize porphyrin of compound-i.

The solvent may be generally used in an amount of 500–1000 times the weight of the compound-h. The reaction temperature is generally set at 20–30° C. The reaction time is generally set at 2–4 hours.

<Step 5> Synthesis of compound-j

The compound-i obtained in the step 4 is dissolved in a solvent such as $CHCl_3$ or benzene. DDQ is added to the resultant solution and allowed to react them to synthesize a porphyrin of compound-j.

The solvent is used in an amount of 500–1000 times the weight of the compound-i. The reaction temperature may be generally set at 20–30° C. The reaction time may be generally set at 5–10 minutes.

<Step 6> Synthesis of compound-k

The compound-j obtained in the step 5 is dissolved in a solvent such as $CHCl_3$ or acetonitrile. A zinc salt (e.g., zinc acetate) dissolved in a solvent is added and stirred to afford a compound-k.

The solvent is generally used in an amount of 500–1000 times the weight of the compound-k. The reaction temperature may be generally set at 20–30° C. The reaction time may be generally set at 0.5–1 hours.

<Step 7> Synthesis of a compound-m

A compound-i is added to the compound-k obtained in the step 6 and dissolved in a solvent such as $CHCl_3$ or acetonitrile. Silver (I) hexafluorophosphate dissolved in an organic solvent is further added to the reaction mixture and stirred. The reaction solution is washed with an aqueous solvent, and the solvent is removed. The residue is dissolved in an acidi-containing organic solvent and stirred. After an aqueous solvent is added, the resultant solution is subjected to extraction with an organic solvent. As a result, the compound-m is obtained.

Chloroform may be used as the non-polar solvent dissolving the compound-k generally in an amount 500–1000 times the weight of the compound-k. Each of the iodine and silver (I) hexafluorophosphate to be added may be used in an molar amount of 0.4–0.6 times the weight of the compound-k.

As the organic solvent dissolving silver (I) hexafluorophosphate, acetonitrile, acetone, or the like may be used in an amount 100–200 times the weight of silver (I) hexafluorophosphate.

The reaction mixture is generally stirred at room temperature for 0.5–1 hour.

As the aquatic solvent for washing the reaction solution, an aqueous solution of sodium bicarbonate, water, or the like may be used.

As the acid-containing organic solvent for dissolving the residue after the washing, any organic solvent capable of reducing the pH value of the reaction mixture to 1 or less. For example, a methanol/concentrated hydrochloric acid (10:1) mixture may be used in an amount 200–500 times the weight of the compound-k. The reaction solution is generally stirred at room temperature for 20–40 minutes.

As the aqueous solvent to be added to the reaction solution obtained, water or the like may be used. As the organic solvent serving as an extractant, chloroform or the like may be used.

The compound-m thus obtained may be washed, if necessary, with an aquatic solvent such as an aqueous solution of sodium bicarbonate or water, purified by chromatography or the like, and subjected to the next step 8.

<Step 8> Synthesis of compound-n

To the compound-m obtained in the step 7 and dissolved in a solvent such as $CHCl_3$ or acetonitrile, a zinc salt (e.g., zinc acetate) dissolved in a solvent is added and stirred.

The solvent may be used generally in an amount 500–1000 times the weight of the compound-m. The reaction temperature may be generally set at 20–30° C. The reaction time may be generally set at 0.5–1 hour.

The compound obtained is washed with water to remove the solvent. The residue is dissolved in an acid-containing organic solvent and stirred. After an aquatic solvent is added to the resultant solution, extraction is performed with an organic solvent. As a result, the compound-n is obtained.

EXAMPLES

Now, examples of the present invention will be explained. However, the present invention will not br limited to these examples.

EXAMPLE 1

Synthesis example of a mercapto-substituted imidazolylporphyrin metal complex dimer represented by the general formula (2) will be explained.

Step 1

Synthesis of 5(1-methyl-2-imidazolyl)-15—(4—(S-acetylthio)phenyl)-10,20-bis(n-heptyl)porphyrin (4)

1-methylimidazol-2-carboaldehyde (1) (27.5 mg, 0.25 mmol), 4—(S-acetylthio)benzaldehyde (2) (45 mg, 0.25 mmol), and dipyromethane(3) (122 mg, 0.5 mmol) were dissolved in chloroform (25 mL). After the atmosphere was substitution with nitrogen, 30 mL of TFA (1.5 equivalent) was added. After the solution was stirred for 2 hours at room temperature, 170 mg of dichlorodicyanobenzoquinone (3 equivalent) was added and stirred for one hour. The resultant mixture was washed with an aqueous solution of sodium bicarbonate and chloroform is removed by distillation, and thereafter, purified by silica gel column chromatography (developing solvent: chloroform:acetone=10:1). As a result, a purple solid material (5 mg, 2.7% yield) was obtained.

MS (TOF) m/e 737.4 (M+1) calculated: 737.39 (M+1); $\lambda_{abs\,(CHCl_3)}$) 418.5, 516.5, 550.5, 591, 649.5 nm; $^1$H NMR (d: CDCl$_3$) –2.67(NH, s, 2H), 0.88(CH$_3$, t), 1.32(CH$_2$, m), 2.49(CH$_2$, m), 2.63(CH$_3$(S-acetyl),s ,3H), 3.40(CH$_3$ (im),s ,3H), 4.95(CH$_2$, m), 7.48(im-4, s, 1H), 7.68(im-5, s, 1H), 7.80(phenyl, d, 1H), 7.81(phenyl, d, 1H), 8.16(phenyl, d, 1H), 8.27(phenyl, d, 1H), 8.78(d, 2H), 8.87(d, 2H), 9.41(d, 2H), 9.45(d, 2H).

Step 2

Synthesis of 5-(1-methyl-2-imidazolyl)-15-(4-(S-acetylthio)phenyl)-10,20-bis(n-heptyl)porphyrin zinc complex (5)

The compound (4)(5 mg, 6.8 mmol) was dissolved in chloroform (0.5 mL) and further a saturated methanol solution of zinc acetate (0.2 mL) was added thereto and stirred at room temperature for 2 hours. The reaction solution was washed with water and the solvent was removed by distillation. The yield of the compound (5) was 4 mg.

MS (TOF) m/e 799.5 (M+1) calculated: 799.31 (M+1); $\lambda_{abs\,(CHCl_3)}$) 414, 438, 567, 621.5 nm; $^1$H NMR (d: CDCl$_3$) 0.88(CH$_2$, m, 4H), 1.00(CH$_3$, t, 6H), 1.50(CH$_2$, m), 1.66 (CH$_3$(im),s ,3H),1.78(CH$_2$, m, 4H), 2.04(CH$_2$, m, 4H), 2.11(im-4, s, 1H)2.68(CH$_3$(S-acetyl),s ,3H), 2.80(CH$_2$, m, 4H), 5.09(CH$_2$, m, 4H), 5.41(d, 2H), 5.51(im-5, s, 1H), 7.81(phenyl, d, 1H), 7.98(phenyl, d, 1H), 8.19(phenyl, d, 1H), 8.72(phenyl, d, 1H), 8.89(d, 2H), 9.04(d, 2H), 9.58(d, 2H).

EXAMPLE 2

Synthesis example of imidazolylporphyrin-quinonylporphyrin dimer represented by the formula (g)

Step 3

Synthesis of 5-(2,5-dimethoxyphenyl)-10,20-bis(heptyl) porphyrin (7)

Formaldehyde (1) (320 mg, 8 mmol) and 2,5-dimethoxybenzaldehyde (6) (166 mg, 1 mmol), dipyromethane (3) (976 mg, 4 mmol) were dissolved in chloroform (200 mL). After substitution of the atmosphere with nitrogen gas was performed, trifluoroacetic acid (80 μL, 0.5 equivalent) was added. The solution mixture was stirred at room temperature. After 70 minutes, dichlorodicyanobenzoquinone (1.35 g, 3 equivalent) was added and stirred for one hour. After washed with an aqueous solution of sodium bicarbonate and chloroform was removed by distillation, the resultant mixture was purified by silica gel column chromatography (developing solvent: CHCl$_3$/hexane=3:1). As a result, a purple solid material (43.4 mg) was obtained in a yield of 6.8%.

MS (TOF) m/e 643.2 (M+1), calculated: 643.39 (M+1); UV visible absorption spectrum (CHCl$_3$) $\lambda_{max}$ 414.5, 512.5, 546.5, 587.5, 643.5 nm; fluorescent spectrum (CHCl$_3$) $\lambda_{max}$ 646, 713 nm ($\lambda_{ext}$ 414 nm); $^1$H NMR (δ:CDCl$_3$) –2.80(NH, s, 2H), 0.85(CH$_3$,t), 1.32(CH$_2$, q), 2.49(CH$_2$, q), 3.49 (OCH$_3$, s, 3H), 3.92(OCH$_3$, s, 3H), 4.95(CH$_2$,m), 7.25(Ar, s,), 7.31(Ar, d, 1H), 7.60(Ar, d, 1H), 8.88(13, 17, d, 2H), 9.33(2, 8, d, 2H), 9.40(12, 18, d, 2H), 9.50(3, 7, d, 2H), 10.04 (15, s, 1H).

Step 4

Synthesis of 5-(2,5-dihydoxyphenyl)-10,20-bis(heptyl) porphyrin (8)

A starting compound (7)(20.5 mg, 31.9 μmol) was dissolved in 2 mL of chloroform. BBr$_3$ (0.2 mL) was added by using a syringe under a nitrogen atmosphere. After stirred for 3 hours at room temperature, the resultant mixture was diluted by adding chloroform little by little to decompose excessive BBr$_3$. The resultant solution was neutralized with an aqueous solution of sodium bicarbonate and then washed with water. After the solvent was removed, the resultant mixture was dried. As a result, the compound (8) (17.1 mg) was obtained in a yield of 87%.

MS (TOF) m/e 615.4 (M+1), calculated: 615.36 (M+1).

Step 5

Synthesis of 5-(2,5-dihydoxyphenyl)-10,20-bis(heptyl) porphyrin (9)

A starting compound (8)(17.1 mg, 27.8 μmol) was dissolved in 1 mL of chloroform. After 20.0 mg of dichlorodicyanobenzoquinone (3 equivalent) was added and stirred for 5 minutes at room temperature, the reaction solution was subjected directly to silica gel column chromatography (developing solvent: CHCl$_3$). As a result, the compound (9) (14.0 mg) was obtained in a yield of 82%.

MS (TOF) m/e 613.2 (M+1), calculated: 613.35 (M+1); UV visible absorption spectrum (CHCl$_3$) $\lambda_{max}$ 411, 508, 586 nm; fluorescent spectrum (CHCl$_3$) $\lambda_{max}$ 644, 710 nm ($\lambda_{ext}$ 411 nm).

Step 6

Synthesis of 5-(2,5-dihydoxyphenyl)-10,20-bis(n-heptyl) porphyrin zinc complex (10)

A starting compound (9)(14.0 mg, 22.8 μmol) was dissolved in 1 mL of chloroform. A saturated methanol solution of zinc acetate (0.3 mL) was added thereto and stirred at room temperature for 30 minutes. The chloroform solution was washed with water and solvent was removed by distillation. As a result, the compound (10) (14.6 mg) was obtained in a yield of 95%.

MS (TOF) m/e 675.0 (M+1), calculated: 675.26 (M+1); UV visible absorption spectrum (CHCl$_3$) $\lambda_{max}$ 417, 546.5 nm; fluorescent spectrum (CHCl$_3$) $\lambda_{max}$ 595, 640 nm ($\lambda_{ext}$ 411 nm).

Step 7

Synthesis of 15-(1-methyl-2-imidazolyl)-15'-(2,5-dihydroxyphenyl)-10,10',20,20'-tetrakis(n-heptyl)-5,5'-bisporphyrin (12)

A compound (10) (14.6 mg, 21.6 μmol) and 5-(1-methyl-2-imidazolyl)-10, 20-bis(n-heptyl)porphyrin zinc complex (11) (83 mg, 127.7 μmol) were dissolved in chloroform (36 mL) and iodine (18.9 mg, 74.7 μmol), $AgPF_6$(18.8 mg, 74.7 μmol) dissolved in 1 mL of acetonitrile were added and stirred at room temperature for 10 minutes. A MALDI-TOF mass spectrum was used for confirming that the starting material was completely consumed and a desired product was produced. Thereafter, a chloroform solvent was washed with an aqueous solution of sodium bicarbonate and water, and removed by distillation under reduced-pressure. The residue was dissolved in 11 mL of methanol/concentrated hydrochloric acid (10:1) and stirred at room temperature for 30 minutes. Water was added to the resultant mixture and the mixture was extracted with chloroform. After drying, a crude product obtained by removing the solvent by distillation under reduced pressure was purified by silica gel column chromatography (developing solvent $CHCl_3$/acetone=10:1). A desired compound was obtained in an amount of 5 mg (35% yield).

MS (TOF) m/e 1199.7 (M+1), calculated: 1197.7 (M+1); UV visible absorption spectrum ($CHCl_3$) $\lambda_{max}$ 412, 452, 523.5, 598 nm; fluorescent spectrum ($CHCl_3$) $\lambda_{max}$ 660, 726 nm ($\lambda_{ext}$ 412 nm); $^1$H NMR(δ: $CDCl_3$) –2.09(NH, s, 4H), 0.83($CH_3$,t, 12H), 1.27($CH_2$, br, 16H), 1.45($CH_2$,br, 8H), 1.73($CH_2$, br, 8H), 2.50($CH_2$, br, 8H), 3.53($CH_3$(Im), s, 3H), 4.90($CH_2$,br, 8H), 7.36(Ar, d, 2H), 7.68(Ar, s, 1H), 7.75(Im-5, s, 1H),7.95–8.05(β position, m, br, 4H) 8.13(β position, d, br, 1H), 8.90(β position, d, 2H), 9.10(β position, m, br, 6H), 9.52 (β position, d, br, 4H).

Step 8

Synthesis of 15-(1-methyl-2-imidazolyl)-15'-(2,5-dihydrroxyphenyl)-10,10',20,20'-tetrakis(n-heptyl)-5,5'-bisporphyrin monozinc complex (13)

The chemical compound (12)(1.5 mg) was dissolved in chloroform (0.2 mL). A saturated methanol solution of zinc acetate (0.05 mL) was added to the mixture and stirred at room temperature for 30 minutes. The resultant solution was washed with water and the solvent was removed by distillation.

The residue was dissolved in chloroform (0.2 mL) and 0.0484 mL (2 equivalent) of a chloroform solution of p-toluene sulfonic acid (0.05 mol/L) was further added. The resultant mixture was washed with an aqueous solution of sodium bicarbonate and then with water. A desired compound (1.6 mg) was obtained in a yield of 100%.

MS (TOF) m/e 1259.6(M+1), calculated: 1259.62 (M+1); UV visible absorption spectrum ($CHCl_3$) $\lambda_{max}$ 416, 456, 561.5 nm; fluorescent spectrum ($CHCl_3$) $\lambda_{max}$ 664, 725 nm ($\lambda_{ext}$ 416 nm).

Measurement Example 1

In poly(imidazolylporphyrin)metal complex having a mercapto group at both ends represented by the general formula (3), it was confirmed that the coordinate bonding of the central metal ion M and a nitrogen atom of an imidazolyl group is dissociated in the presence of a polar solvent and linked in the absence of the polar solvent.

FIG. 1 is a chromatogram of a solution prepared by blending a polyporphyrin (the formula (e)) whose molecular weight distributed to 500,000 with a peak of 100,000, and a dimer of acetylthiophenyl-imidazolylporphyrin zinc complex (the general formula (2)) in a ratio of 5:1 in ethanol-free chloroform. Since the absorption coefficient at a detection wavelength of 415 nm of the two compounds differs, the peak-intensity ratio does not correspond to the mix ratio of the two compounds.

After methanol is added to the above-obtained solution mixture, the solvent is removed. The resultant mixture is redissolved in ethanol-free chloroform. The solution thus prepared is subjected to chromatography. The chromatogram is shown in FIG. 2.

In the case where both compounds are simply mixed in chloroform, they are separately detected as shown in FIG. 1. FIG. 1 therefore demonstrates that stable bonding between zinc ion and imidazolyl group in a complementarily coordinated dimer cannot perform dissociation/reconstruction.

Figure 2:
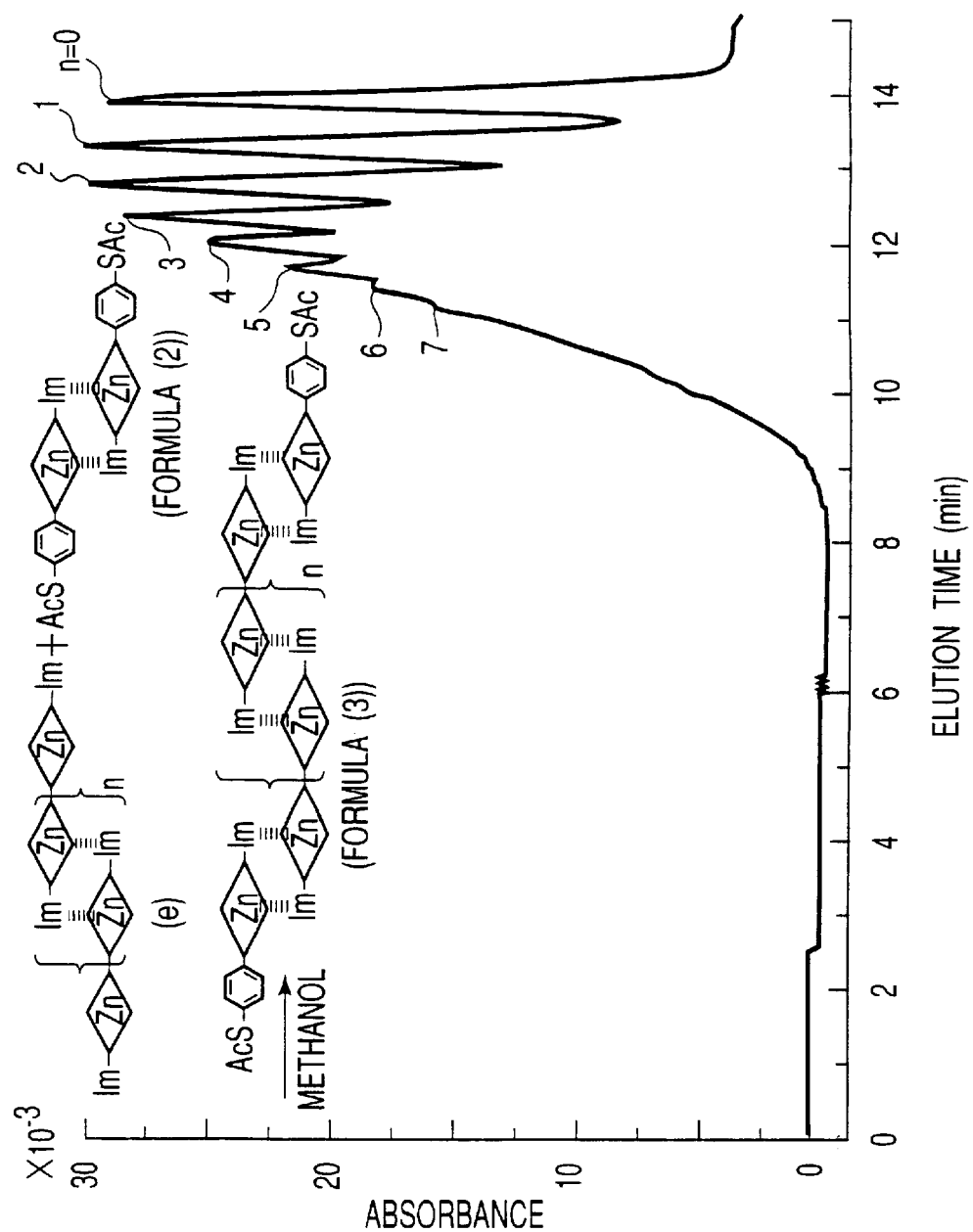
FIG. 2 is a chromatogram of a solution containing the poly(porphyrin) of the formula (e) and a dimer of an acetylthiophenyl-imidazolylporphyrin zinc complex represented by a general formula (2), which are redissolved in ethanol-free chloroform. The solution is prepared first by adding methanol to the mixture of the poly(porphyrin) and the dimer, removing a solvent therefrom, and redissolving the resultant mixture in the ethanol-free chloroform.

On the other hand, the chromatogram of FIG. 2 of the solution treated with methanol demonstrates that poly (porphyrin) having a molecular weight of 40,000 or more almost disappears, whereas electric wires differs in length (n of 0–7) are independently detected. Therefore, it is clear that the chain length of the molecule can be controlled by setting the polarity of the solvent properly. This suggests that these wires can be separated into wires of desired lengths. In other words, they are treated as a stable single compound in a non-polar solvent such as chloroform as shown in FIG. 1, whereas they can be converted into another wires having different molecular length by treatment with a polar solvent such as ethanol.

According to the present invention, there is provided an imidazolylporphyrin metal complex monomer represented by the general formula (1). The metal atom of the monomer can be coordinated to a nitrogen atom of an imidazolyl group of another monomer to form cross-linking between the porphyrins. In this manner, an imidazolylporphyrin dimer represented by the general formula (2) can be obtained.

Poly(Imidazolylporphyrin metal complex) having a mercapto group at both ends (the general formula (3)) is a polymer having a dimer of the general formula (2) as a constitutional unit and having an acetylthio group at both ends. In addition, the poly(imidazolylporphyrin metal complex) represented by the general formula (4) is a polymer having the dimer represented by the general formula (2) as a constitutional unit and having an acetylthio group at one end of the polymer and a quinonyl group at the other end of the polymer. In the dimer of the general formula (2), the coordinate bonding between the metal atom and a nitrogen atom of the imidazolyl group can be constructed or cleaved by controlling the polarity of a solvent by, for example, using a high polar solvent such as methanol.

The poly(imidazolylporphyrin metal complex) of the general formula (3) and poly(imidazolylporphyrin metal complex) of the general formula (4) may be used as molecular-level electric wire filaments different in length in the submicron order. Furthermore, the complex of the general formula (4) may be applied to wire through which light excitation energy flows. Since the acetylthio group at both ends binds to a gold electrode to form a strong Au—S bond, the poly(imidazolylporphyrin metal complex) of the present invention may be used as a photoconductive device, an electron transfer medium, and an energy transfer medium.

Particularly, in the poly(imidazolylporphyrin metal complex) of the general formula (4) having a mercapto group at one end and a quinonyl group at the other end, the quinonyl group serves as an electron acceptor. Therefore, an electron can be transferred through the polymer chain (array) of the poly(imidazolylporphyrin metal complex). Furthermore, it is possible to construct an energy transfer system of a center of photosynthesis consisting of an antenna complex, a special pair, pheophytin and quinone. Therefore, it is expected that poly(imidazolylporphyrin metal complex) of the general formula (4) is used to construct an artificial photosynthetic system.

The electron-transportation using light excitation may be used in a solar battery. In the solar battery, one end of the polymer wire is linked to a gold electrode via a thiol group, as described in the present invention. When the porphyrin portion of the polymer is excited with light, a current flows through the polymer wire which acts like a carrier. Therefore, a novel solar battery excellent in efficiency may be developed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A mercapto-substituted imidazolylporphyrin metal complex monomer represented by formula (1):

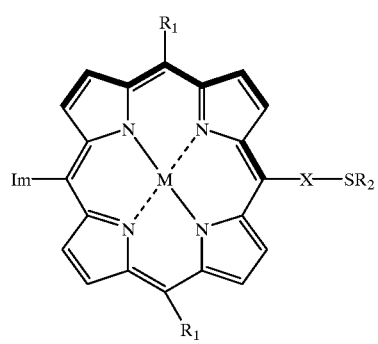

(1)

wherein $R_1$ represents a group selected from the group consisting of an alkyl group, unsubstituted aryl group, alkyl-substituted aryl group and alkyloxy-substituted aryl group; M represents a metal ion selected from the group consisting of Zn(II), GA(III), Fe(II), Co(II), and Ru(II): X represents a divalent linking group consisting of one or more group selected from the group consisting of an arylene group and an alkylene group; $R_2$ represents a hydrogen atom or an acetyl group; and Im represents $Im_1$ and $Im_2$ set forth below:

Im =

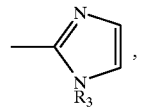

($Im_1$)

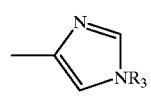

($Im_2$)

wherein $R_3$ represents a hydrogen atom or an alkyl group.

2. The monomer represented by formula (1) according to claim 1, wherein $R_1$ represents a group selected from the group consisting of an alkyl group having 3–20 carbon atoms, aryl group having 6–20 carbon atoms, alkyl-substituted aryl group having 7–24 carbon atoms and alkoxy-substituted aryl group having 7–24 carbon atoms; X represents a divalent linking group consisting of one or more group selected from the group consisting of —$(CH_2)_n$— (wherein n represents an integer of 1–17) and an arylene group having 6–14 carbon atoms.

3. The monomer represented by formula (1) according to claim 1, wherein $R_1$ is an alkyl group having 3–20 carbon atoms; M is Zn ion; $R_2$ is an acetyl group; and Im is $Im_1$ (wherein $R_3$ is a methyl group).

4. A mercapto-substituted imidazolylporphyrin metal complex dimer represented by formula (2):

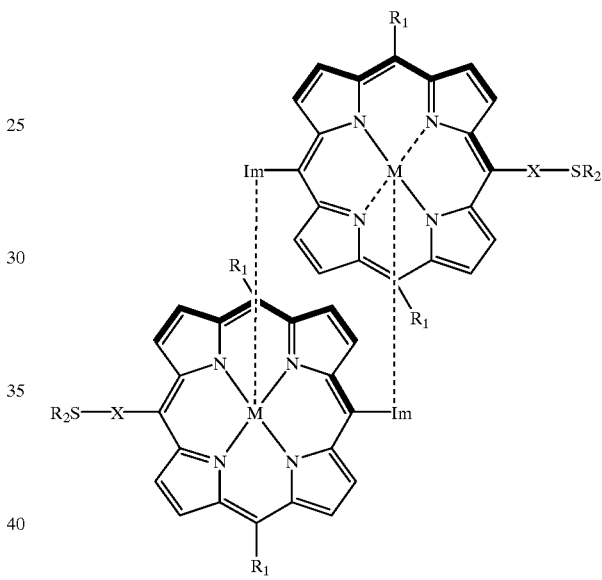

(2)

wherein each of $R_1$, M, $R_2$, X and Im including $R_3$ has the same meaning as those defined in claim 1, respectively.

5. The dimer according to claim 4, wherein $R_1$ represents a group selected from the group consisting of an alkyl group having 3–20 carbon atoms, aryl group having 6–20 carbon atoms, alkyl-substituted aryl group having 7–24 carbon atoms and alkyloxy-substituted aryl group having 7–24 carbon atoms; X represents a divalent linking group consisting of one or more group selected from the group consisting of —$(CH_2)_n$— (wherein n represents an integer of 1–17) and an arylene group having 6–14 carbon atoms.

6. The dimer according to claim 4, wherein $R_1$ is an alkyl group having 3–20 carbon atoms; M is Zn ion; X is a phenylene group; $R_2$ is an acetyl group; and Im is $Im_1$ (wherein $R_3$ is a methyl group).

7. A poly(imidzolylporphyrin metal complex) having a mercapto group at both ends thereof, which is represented by formula (3):

(3)

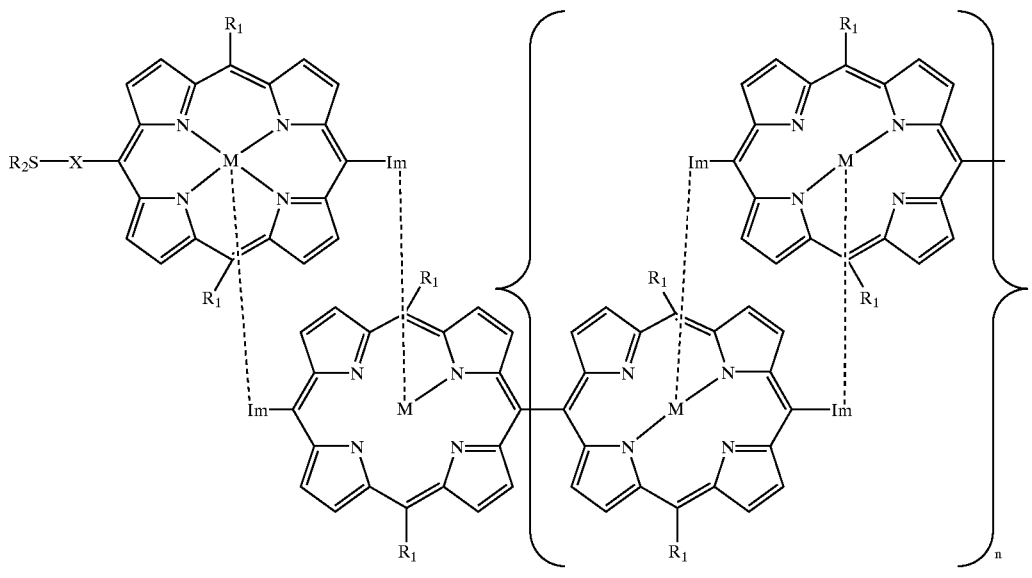

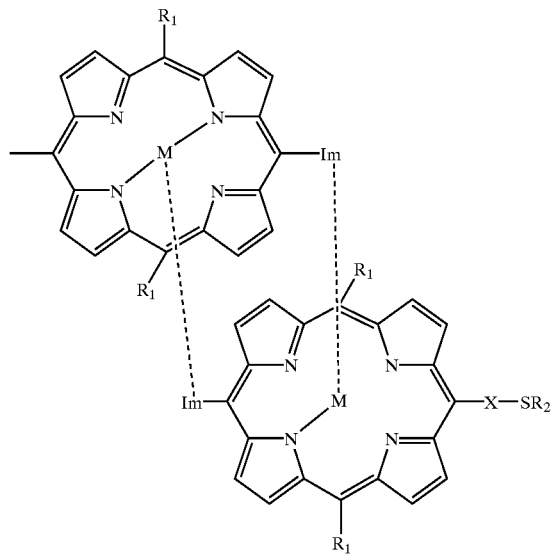

wherein each of $R_1$, M, $R_2$, X and Im including $R_3$ has the same meaning as those defined in claim 1, respectively; and n represents an integer of 0 or more.

8. The poly(imidazolylporphyrin metal complex) represented by formula (3) according to claim 7, wherein $R_1$ represents a group selected from the group consisting of an alkyl group having 3–20 carbon atoms, aryl group having 6–20 carbon atoms, alkyl-substituted aryl group having 7–24 carbon atoms and alkyloxy-substituted aryl group having 7–24 carbon atoms; X represents a divalent linking group consisting of one or more group selected from the group consisting of —$(CH_2)_n$— (wherein n represents an integer of 1–17) and an arylene group having 6–14 carbon atoms.

9. The poly(imidazolylporphyrin metal complex) represented by formula (3) according to claim 7, wherein $R_1$ is an alkyl group having 3–20 carbon atoms; M is Zn ion; X is a phenylene group; $R_2$ is an acetyl group; and Im is $Im_1$ (wherein $R_3$ is a methyl group).

10. A poly(imidazolylporphyrin metal complex) having a mercapto group at one end and a quinonyl group at the other end, which is represented by formula (4):

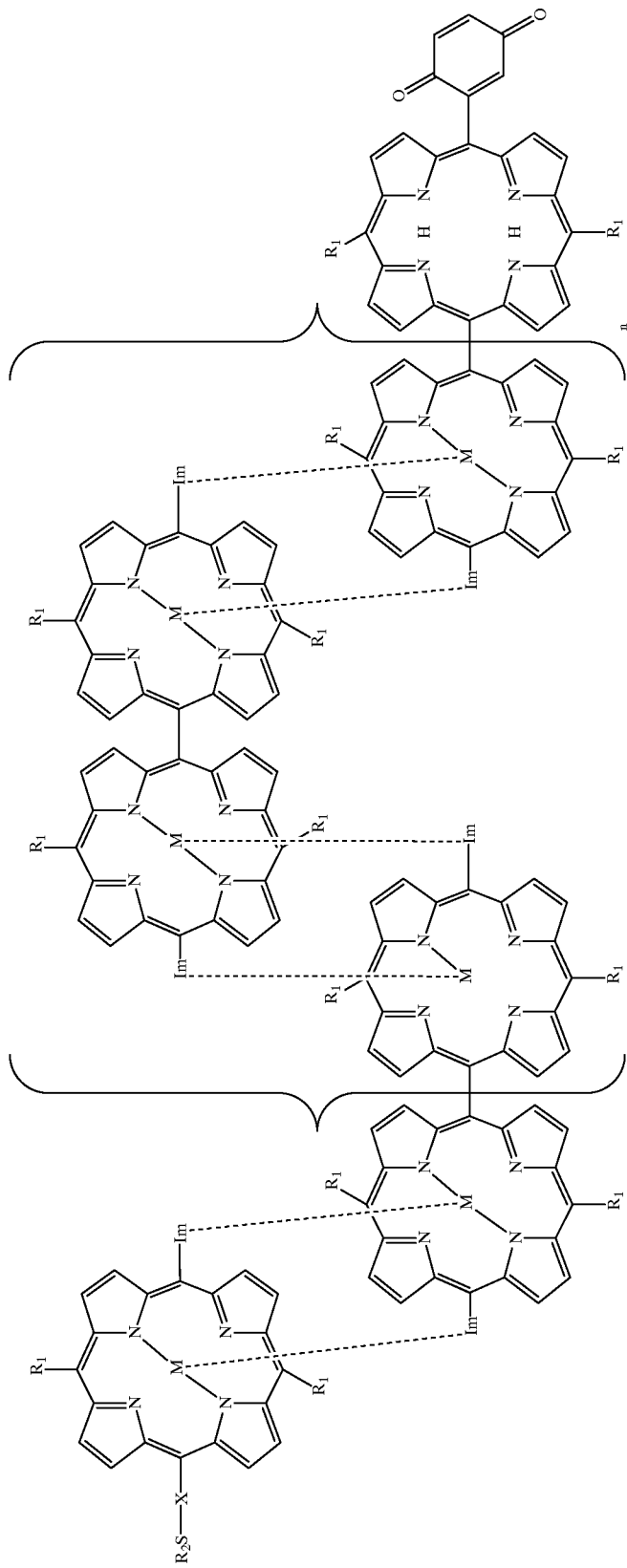
(4)

wherein each or $R_1$, M, $R_2$, X and Im including $R_3$ has the same meaning as those defined in claim 1, respectively; and n represents an integer of 0 or more.

11. The poly(imidazolylporphyrin metal complex) represented by formula (4) according to claim 10, wherein $R_1$ represents a group selected from the group consisting of an alkyl group having 3–20 carbon atoms, aryl group having 6–20 carbon atoms, alkyl-substituted aryl group having 7–24 carbon atoms; X represents a divalent linking group consisting of one or more group selected from the group consisting of —$(CH_2)_n$— (wherein n represents an integer of 1–17) and an arylene group having 6–14 carbon atoms.

12. The poly(imidazolylporphyrin metal complex) represented by formula (4) according to claim 10, wherein $R_1$ is an alkyl group having 3–20 carbon atoms; M is Zn ion; X is a phenylene group; $R_2$ is an acetyl group; and Im is $Im_1$ (wherein $R_3$ is a methyl group).

13. A method for preparing a porphyrin metal complex dimer represented by formula (2)

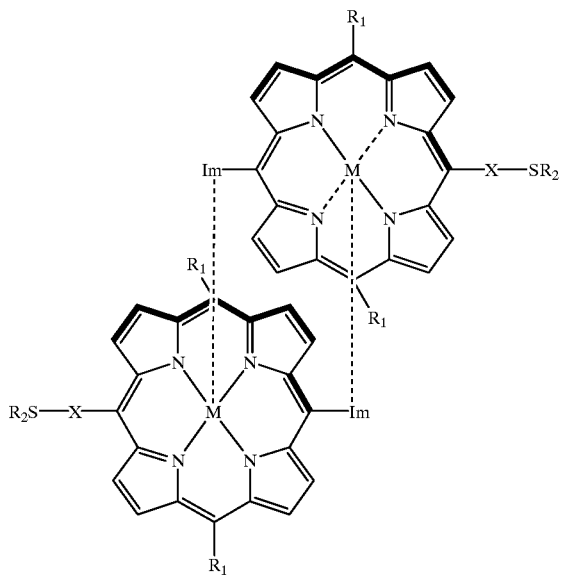

(I) reacting compounds-a to -c:

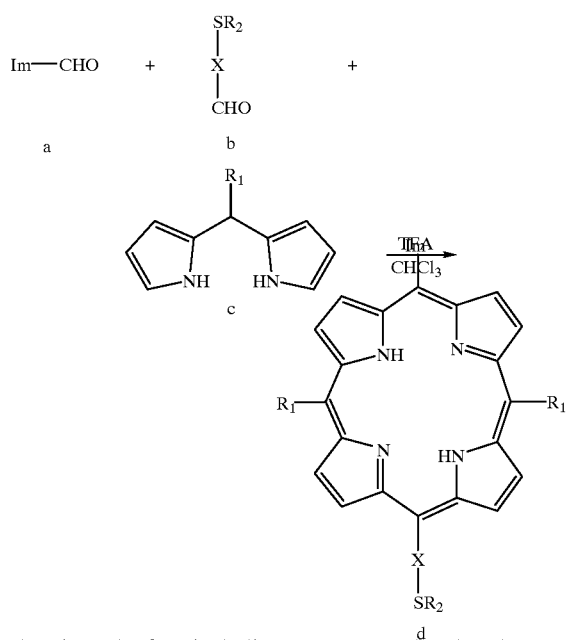

wherein each of Im including $R_3$, X, $R_1$ and $R_2$ has the same meaning as those defined in claim 1, respectively, with trifluoroacetic acid thereby obtaining a porphyrin of compound d (wherein each of Im including $R_3$, X, $R_1$ and $R_2$ has the same meaning as those defined in claim 1); and (ii) inserting a metal ion of M (wherein M has the same meaning as that defined in claim 1, respectively), into the porphyrin of compound d:

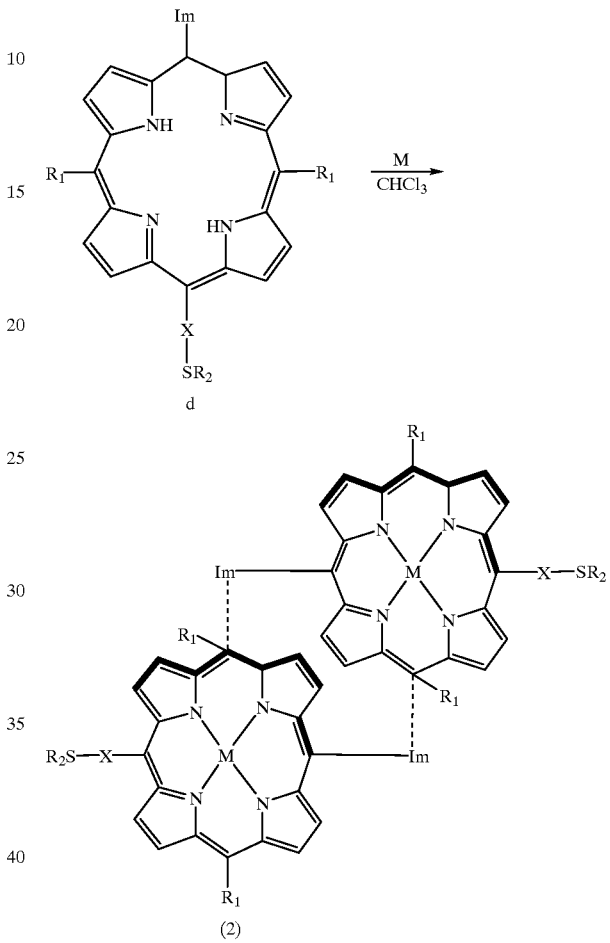

thereby obtaining the porphyrin metal complex dimer represented by formula (2), wherein the steps (i) and (ii) are performed in a solvent having low polarity.

14. A method for preparing a porphyrin metal complex monomer represented by formula (1):

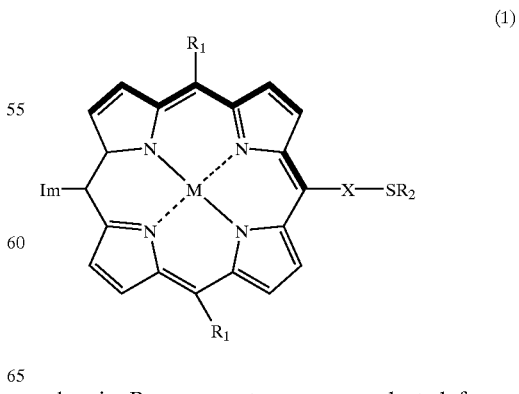

wherein $R_1$ represents a group selected from the group consisting of an alkyl group, unsubstituted aryl group, alkyl-substituted aryl group and alkyloxy-substituted aryl group; M represents a metal ion selected from the group consisting of Zn(II), Ga(III), Fe(II), Co(II), and Ru(II): X represents a divalent linking group consisting of one or more group selected from the group consisting of an arylene group and an alkylene group; $R_2$ represents a hydrogen atom or an acetyl group; and Im represents $Im_1$ and $Im_2$ set forth below:

Im =

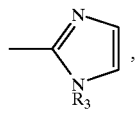 ($Im_1$),

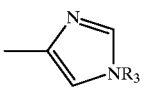 ($Im_2$)

wherein $R_3$ represents a hydrogen atom or an alkyl group, comprising dissolving a mercapto-substituted imidazolylporphyrin metal complex dimer represented by formula (2):

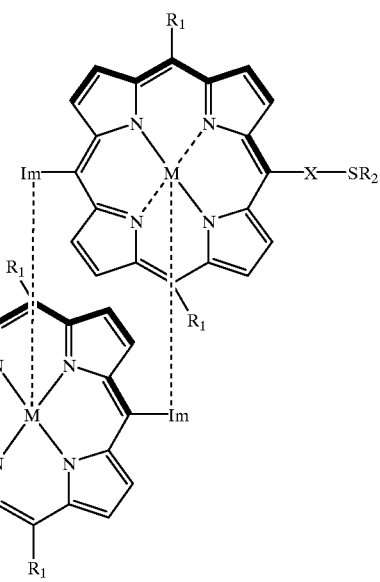

(2)

wherein each of $R_1$, M, $R_2$, X and Im including $R_3$ has the same meaning as defined above, in a solvent having high polarity.

15. A method of preparing poly(imidazolylporphyrin metal complex) represented by formula (3):

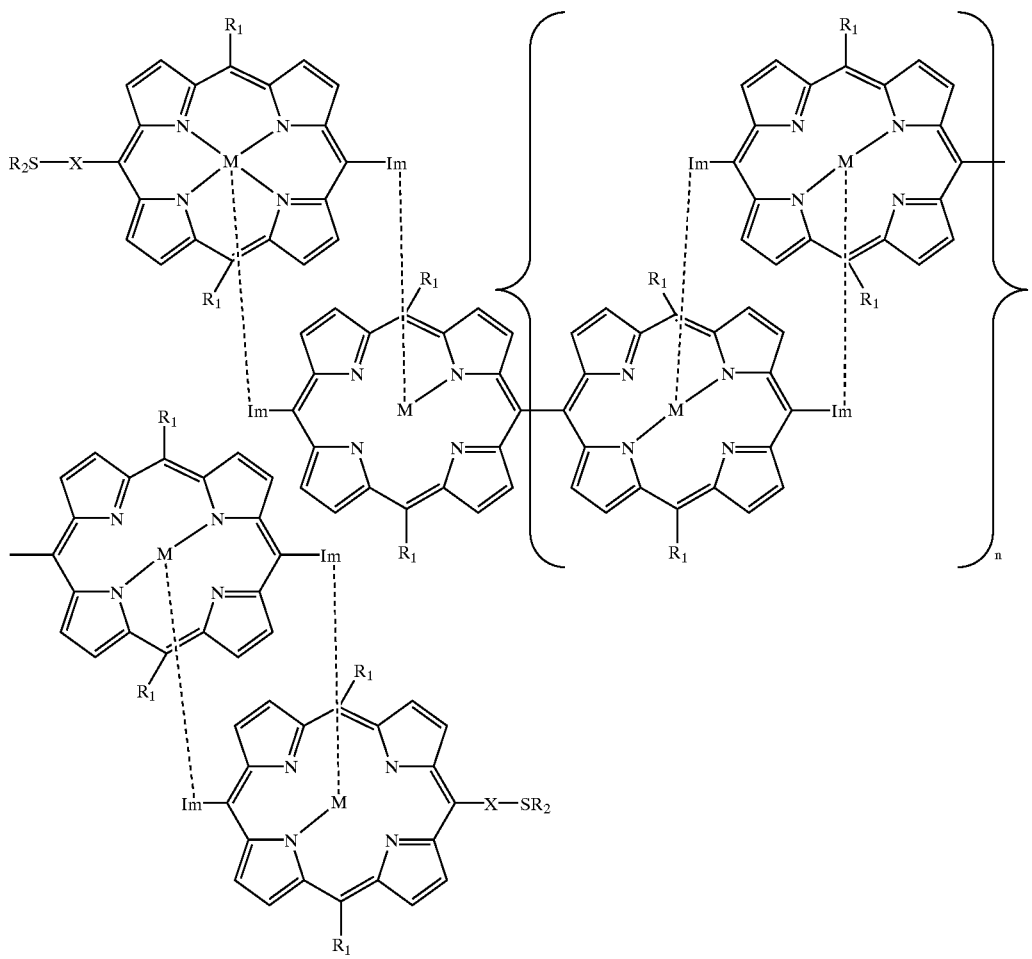

(3)

wherein each of $R_1$, M, $R_2$, X and Im including $R_3$ has the same meaning as those defined in claim 1, respectively; and n represents an integer of 0 or more, comprising:

(i) dissolving a porphyrin metal complex dimer represented by formula (2):

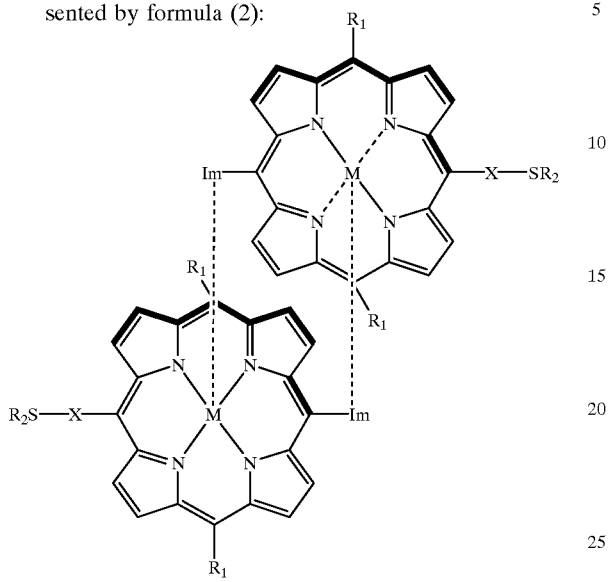

wherein each of $R_1$, M, $R_2$, X and Im including $R_3$ has the same meaning as those defined in claim 1, respectively and a poly(imidazolylporphyrin) represented by formula (e):

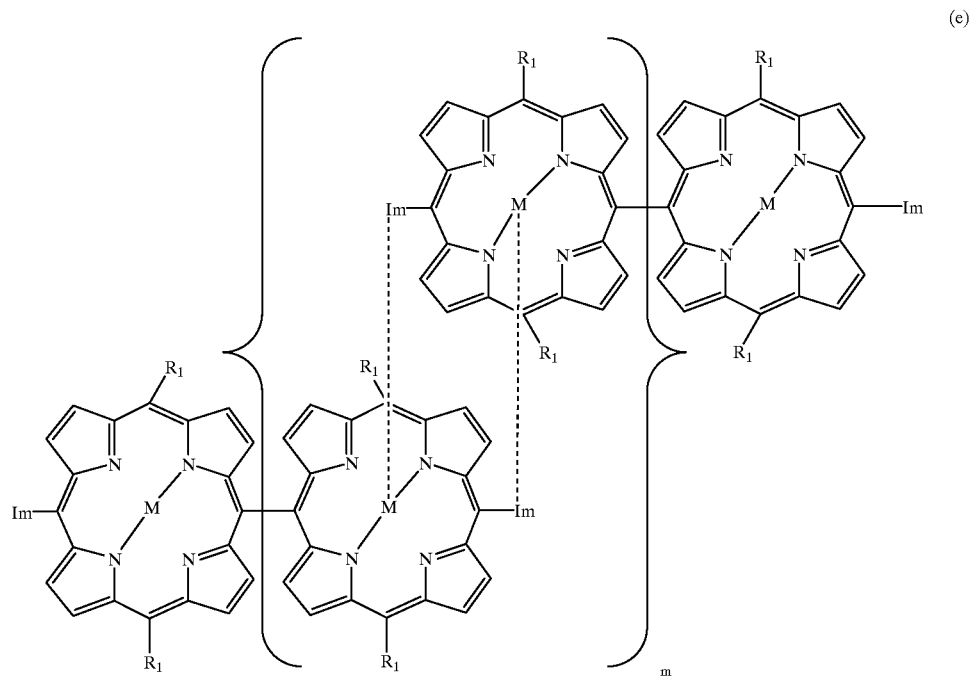

wherein each of $R_1$, Im including $R_3$, and M has the same meaning as those defined in claim 1, and m represents an integer of 0 or more, in a solvent having high polarity; and then (ii) reducing the polarity of the solvent.

16. A method of preparing the porphyrin represented by formula (4):

(4)
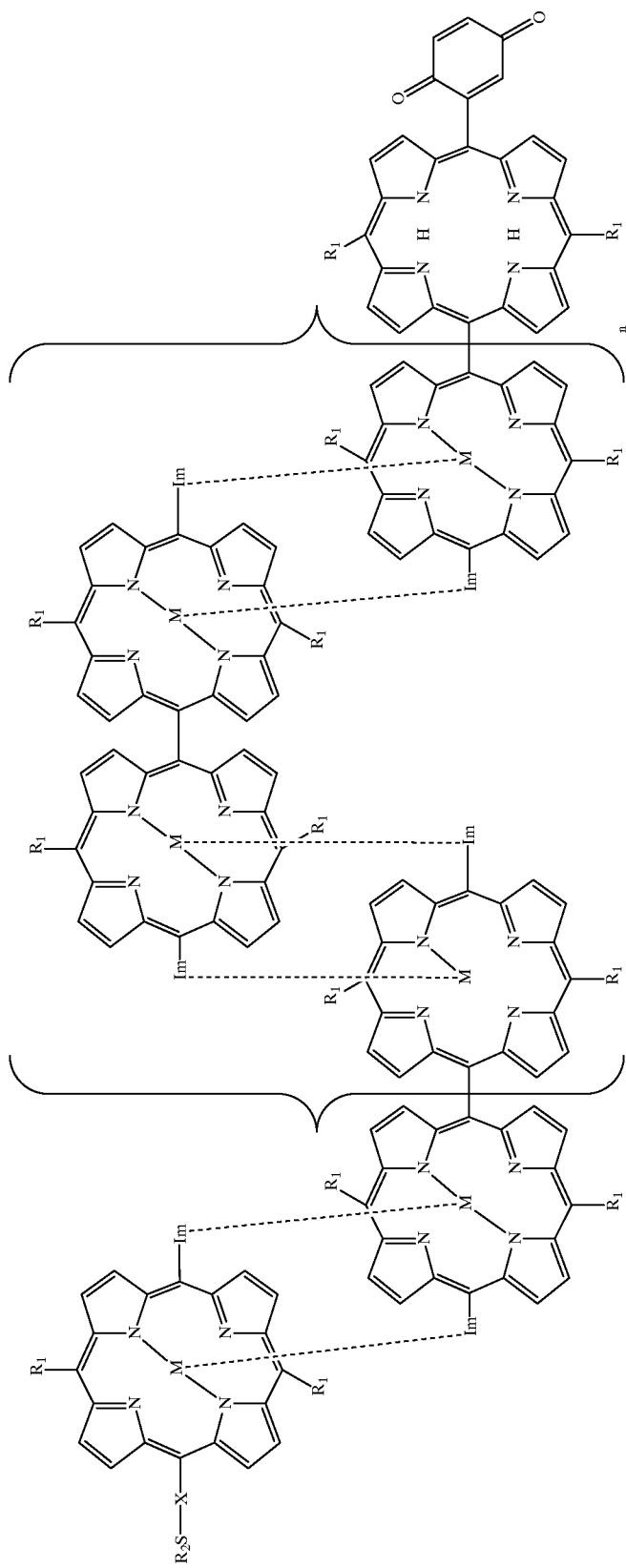

wherein each of $R_1$, M, $R_2$, X and Im including $R_3$ has the same meaning as those defined in claim 1, respectively; and n represents an integer of 0 or more, comprising:

mixing a poly(imidazolylporphyrin) having a mercapto group at one end thereof, which is represented by formula (f)

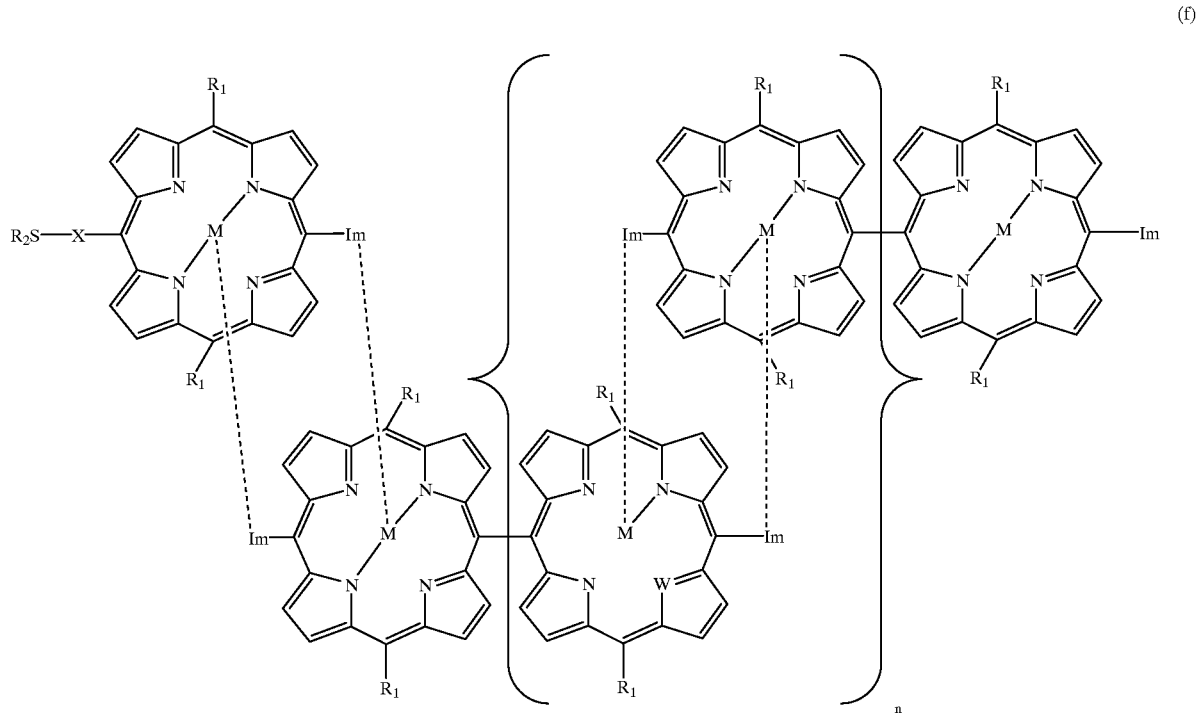

(f)

wherein each of $R_1$, $R_2$, Im including $R_3$ and M has the same meaning as those defined in claim 1, respectively; and n is an integer of 0 or more, and a imidazolylporphyrin-quinonylporphyrin dimer represented by a formula (g):

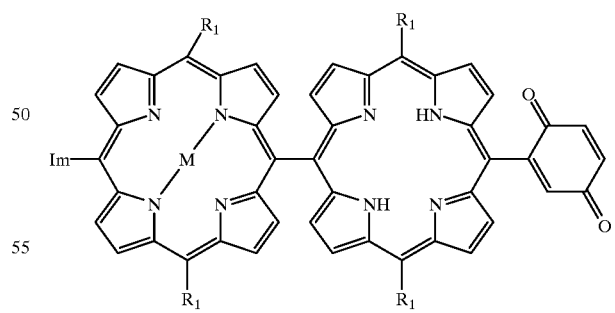

(g)

wherein each of $R_1$, Im including $R_3$, and M has the same meaning as those defined in claim 1, respectively, in a solvent whose polarity is controlled.

* * * * *